US012589111B2

(12) United States Patent
Liu et al.

(10) Patent No.: US 12,589,111 B2
(45) Date of Patent: Mar. 31, 2026

(54) PT(IV) CHEMOTHERAPEUTIC PRODRUG AND CONTROLLED RELEASE THEREOF FOR TREATMENT OF TUMORS

(71) Applicant: PEKING UNIVERSITY, Beijing (CN)

(72) Inventors: Zhibo Liu, Beijing (CN); Qunfeng Fu, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 276 days.

(21) Appl. No.: 18/038,629

(22) PCT Filed: Nov. 24, 2021

(86) PCT No.: PCT/CN2021/132886
§ 371 (c)(1),
(2) Date: May 24, 2023

(87) PCT Pub. No.: WO2022/111541
PCT Pub. Date: Jun. 2, 2022

(65) Prior Publication Data
US 2024/0009230 A1 Jan. 11, 2024

(30) Foreign Application Priority Data
Nov. 25, 2020 (CN) ........................ 202011337782.X

(51) Int. Cl.
*A61K 33/243* (2019.01)
*A61K 31/282* (2006.01)
(Continued)

(52) U.S. Cl.
CPC .......... *A61K 33/243* (2019.01); *A61K 31/282* (2013.01); *A61K 41/0038* (2013.01);
(Continued)

(58) Field of Classification Search
CPC .................................................... A61K 33/243
See application file for complete search history.

(56) References Cited

U.S. PATENT DOCUMENTS

2017/0081352 A1* 3/2017 Benita ..................... A61P 35/00
2017/0246182 A1 8/2017 Sessler et al.
(Continued)

FOREIGN PATENT DOCUMENTS

CN 105622674 A 6/2016
CN 106471006 A 3/2017
(Continued)

OTHER PUBLICATIONS

Babak, M.V., et al., "Dual-targeting dual-action platinum(iv) platform for enhanced anticancer activity and reduced nephrotoxicity", Angewandte Chemie International Edition, Apr. 23, 2019, pp. 8109-8114, vol. 58, No. 24.
(Continued)

*Primary Examiner* — Benjamin J Packard
(74) *Attorney, Agent, or Firm* — Scully, Scott, Murphy & Presser, P.C.

(57) ABSTRACT

Provided is a Pt(IV) complex. As a prodrug, the Pt(IV) complex is activated by irradiation to release a Pt(II) complex for the treatment of tumors. Also provided is a pharmaceutical composition including the Pt(IV) complex, and the use of the Pt(IV) complex in the preparation of a drug for treating tumors by means of irradiation activation. Further provided is a kit including the Pt(IV) complex and the description, wherein the description indicates that radiotherapy is performed after administration to treat tumors.

13 Claims, 3 Drawing Sheets

(51) Int. Cl.
*A61K 41/00* (2020.01)
*A61K 51/04* (2006.01)
*A61P 35/00* (2006.01)
*C07F 15/00* (2006.01)

(52) U.S. Cl.
CPC .......... *A61K 51/0482* (2013.01); *A61P 35/00* (2018.01); *C07F 15/0093* (2013.01); *A61K 2121/00* (2013.01)

(56) References Cited

U.S. PATENT DOCUMENTS

| | | | |
|---|---|---|---|
| 2018/0008614 | A1 | 1/2018 | Bilodeau et al. |
| 2018/0354979 | A1 | 12/2018 | Kowol et al. |

FOREIGN PATENT DOCUMENTS

| | | | |
|---|---|---|---|
| CN | 106572991 | A | 4/2017 |
| CN | 108368143 | A | 8/2018 |
| CN | 109438522 | A | 3/2019 |
| CN | 116635396 | A | 8/2023 |
| JP | 2017510994 | A | 4/2017 |
| JP | 2017522377 | A | 8/2017 |
| JP | 2018538292 | A | 12/2018 |
| WO | 2011143201 | A2 | 11/2011 |
| WO | 2015166498 | A1 | 11/2015 |
| WO | 2015191797 | A1 | 12/2015 |
| WO | 2017097986 | A1 | 6/2017 |
| WO | 2017115372 | A1 | 7/2017 |
| WO | 2020190907 | A1 | 9/2020 |

OTHER PUBLICATIONS

Chin, C.F., et al., "Ratiometric delivery of Cisplatin and doxorubicin using tumour-targeting carbon-nanotubes entrapping platinum(iv) prodrugs", Chem. Sci., 2014, pp. 2265-2270, vol. 5, No. 6.

Li, X., et al. "Current developments in PT(IV) prodrugs conjugated with bioactive ligands", Bioinorganic Chemistry and Applications, Oct. 2018, pp. 1-18, vol. 2018, Article ID 8276139.

Liu, J., et al. "Nanoscale-coordination-polymer-shelled manganese dioxide composite nanoparticles: A multistage redox/ph/h2O2-responsive cancer theranostic nanoplatform", Advanced Functional Materials, 2017, pp. 1-11, 1605926.

Ma, L., et al., "Monochalcoplatin: An Actively Transported, Quickly Reducible, and Highly Potent PtIV, Anticancer Prodrug", Angew Chem Int. Ed., 2018, pp. 9098-9102, 57.

Pathak, R.K., et al., "A designer bow-tie combination therapeutic platform: An approach to resistant cancer treatment by simultaneous delivery of cytotoxic and anti-inflammatory agents and radiation", Biomaterials, Dec. 2018, pp. 117-129, vol. 187.

Xiao, H., et al., "Photosensitive Pt(IV)-azide prodrug-loaded nanoparticles exhibit controlled drug release and enhanced efficacy in vivo", Journal of Controlled Release, 2013, pp. 11-17, vol. 173.

Zhang, R., et al., "Catalase-loaded cisplatin-prodrug-constructed liposomes to overcome tumor hypoxia for enhanced chemo-radiotherapy of cancer." Biomaterials, 2017, pp. 13-21, vol. 138.

Zheng, Y.-R, et al., "Pt(iv) prodrugs designed to bind non-covalently to human serum albumin for drug delivery", Journal of the American Chemical Society, Jun. 2014, pp. 8790-8798, vol. 136.

Zhang, M., et al., "Nanoparticle co-delivery of wortmannin and cisplatin synergistically enhances chemoradiotherapy and reverses platinum resistance in ovarian cancer models", Biomaterials (2018), Accepted Mar. 31, 2018, Available online Mar. 31, 2018, pp. 1-10, 169.

Tan, X., et al., "Small Molecular Platinum (IV) Compounds as Antitumor Agents", Progress in Chemistry 2018, pp. 831-846, vol. 30, Issue 6 (with English abstract).

Merkul, E., et al., "A successful search for new, efficient, and silverfree manufacturing processes for key platinum(II) intermediates applied in antibody-drug conjugate (ADC) production", Green Chem., 2020, Accepted Dec. 20, 2019, pp. 2203-2212, 22.

Bednarski P.J. et al., "Photoactivatable Platinum Complexes", Anti-Cancer Agents in Medicinal Chemistry 7(1):75-93 (Jan. 2007) (cited in EP OAs 040 & 041).

Burroughs P. et al., "Radiation Damage in Some Platinum(IV) Complexes Produced During Soft X-Ray Photoelectron Spectroscopic Studies", Journal of the Chemical Society Faraday Transactions 2 Molecular and Chemical Physics. 71:177-187 (Jan. 1975) (cited in CN OA).

Fu Q. et al., "Radiotherapy-Triggered Reduction of Platinum-Based Chemotherapeutic Prodrugs in Tumours", Nature Biomedical Engineering 8:1425-1435 (Nov. 2024) (cited in CN OA).

Kolbeck C. et al., "Redox Chemistry, Solubility, and Surface Distribution of Pt(II) and Pt(IV) Complexes Dissolved in Ionic Liquids", Journal of Molecular Liquids 192:103-113 (Jul. 2014) (cited in CN OA).

MacKay F.S. et al., "A Potent Cytotoxic Photoactivated Platinum Complex", PNAS 104(52):20743-20748 (Dec. 26, 2007) (cited in EP OA 041).

Chinese Office Action dated Jul. 9, 2025 received in Chinese Patent Application No. 202180079479.0, together with an English-language translation.

European Office Action dated Aug. 12, 2025 received in European Application No. 21 897 040.8.

European Office Action dated Aug. 12, 2025 received in European Application No. 21 897 041.6.

* cited by examiner

PT(IV) CHEMOTHERAPEUTIC PRODRUG AND CONTROLLED RELEASE THEREOF FOR TREATMENT OF TUMORS

FIELD OF THE INVENTION

The present disclosure belongs to the field of medicinal chemistry. Specifically, the present disclosure relates to a Pt(IV) chemotherapeutic prodrug and its controlled release for treating tumors.

BACKGROUND OF THE INVENTION

Cancer is one of the most serious contemporary diseases that threaten human life and health. Surgery, radiotherapy and chemotherapy are collectively referred to as the three major methods for treating tumors.

Radiation therapy is a local treatment method that uses radiation to treat tumors. The curative effect of radiotherapy depends on radiosensitivity, and different tissues and organs and various tumor tissues have different responses of changes after being irradiated. For example, fibrosarcoma, osteosarcoma, and melanoma are radiation-insensitive (resistant) tumors. Radiation therapy is difficult to kill all the cancer cells in the tumor, and has very limited killing effect on hypoxic cancer cells.

Chemotherapy uses chemical drugs to kill cancer cells for treatment purposes. Divalent platinum-based drugs have high-efficiency and broad-spectrum anticancer activity, and have become clinically important first-line chemotherapy drugs. Divalent platinum-based drugs are widely used in the treatment of common malignant tumors such as lung cancer, bladder cancer, ovarian cancer, cervical cancer, esophageal cancer, gastric cancer, colorectal cancer and head and neck tumors. The first generation of platinum-based anticancer drugs is represented by Cisplatin, the second generation of platinum-based anticancer drugs is represented by Carboplatin and Nedaplatin. and the third generation of platinum-based anticancer drugs is represented by Oxaliplatin and Lobaplatin. The side effects of divalent platinum-based drugs, such as nephrotoxicity, gastrointestinal toxicity, hematological system toxicity, nervous system toxicity and ototoxicity, limit their application, and the drug resistance of tumors also limits their therapeutic effect. In order to expand platinum-based drugs, studies on tetravalent platinum drugs have also been carried out. Tetravalent platinum compounds themselves have low killing ability to cancer cells, and can exert anticancer activity by being reduced and releasing divalent platinum under physiological conditions. Tetravalent platinum compounds not only retain the broad-spectrum and high-efficiency anticancer advantages of traditional divalent platinum drugs, but also bring other unique advantages because of the coordination structure of tetravalent platinum different from divalent platinum. Tetravalent platinum has a $d^2sp^3$ hexa-coordination structure, and has stability stronger than that of divalent platinum, thereby having higher blood stability. The tetravalent platinum complex possesses two additional ligands in the axial direction, which provides more options for the design of platinum-based drugs. However, although some tetravalent platinum complexes such as iproplatin or satraplatin entered clinical research in the last century, there is still no tetravalent platinum drug approved for marketing.

Therefore, there is still a need to develop a platinum drug and/or a platinum drug-based treatment regimen with lower toxicity and higher efficacy.

SUMMARY OF THE INVENTION

After in-depth research and creative work, the present inventors found that Pt(IV) complexes can be used as prodrugs, and the prodrugs release divalent platinum drugs through irradiation to realize the treatment of tumors. If radiotherapy and Pt(IV) complexes are combined efficiently, that is, radiation activation is used to control the release of Pt(IV) complexes, the therapeutic effect can be effectively improved.

In one aspect, the present disclosure provides a Pt(IV) complex of formula (I), which is used as a prodrug to treat a tumor through irradiation activation, (I)

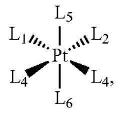

wherein $L_1$ to $L_6$ are ligands of platinum; the complex can release $L_5$ and $L_6$ to obtain a Pt(II) complex of formula (II) after irradiation, (II)

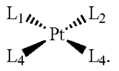

Optionally, the Pt(II) complex of formula (II) is a cis-configuration Pt(II) complex. For example, the Pt(II) complex of formula (II) is Cisplatin, Carboplatin, Nedaplatin, Oxaliplatin, Lobaplatin, Heptaplatin, Cycloplatin, Miboplatin, Enloplatin, Sebriplatin, Spiroplatin, Zeniplatin, TRK-710, Aroplatin, bis(isopropylamine)platinum(II) dichloride, or bis(cyclopentylamine)platinum(II) dichloride. In a preferred embodiment, the Pt(II) complex of formula (II) is Cisplatin, Carboplatin, Nedaplatin, Oxaliplatin. Lobaplatin, or Heptaplatin.

Optionally, $L_5$ and $L_6$ are each independently —OC(O)—R, wherein R is selected from optionally substituted $C_{1-20}$ alkyl, optionally substituted $C_{1-20}$ alkyloxy and optionally substituted amino, wherein the substituent is selected from $C_{1-18}$ alkyl, carboxyl, hydroxyl, halogen, mercapto, amino, di-$C_{1-3}$ alkylamino, carbonyl, phenyl, halogenated phenyl, $C_{1-6}$ alkyl-substituted phenyl, a maleimide group, and triphenylphosphonium. For example, each R is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, eicosyl, carboxymethylene, 2-carboxyethylene, 3-carboxypropylene, 4-carboxybutylene, 5-carboxypentylene, 6-carboxyhexylene, (dimethylamino)methylene, 2-(dimethylamino)ethylene, 3-(dimethylamino)propylene, 4-(dimethylamino)butylene, 5-(dimethylamino)pentylene, 6-(dimethylamino)hexylene, 5-maleimidopentylene, 6-maleimidohexylene, 7-maleimidoheptylene, 8-maleimidooctylene, 3-(4-iodophenyl)propylene, 3-(3-iodophenyl)propylene, 3-(3,5-diiodophenyl)propylene, 3-(4-bromophenyl) propylene, 3-(3-bromophenyl)propylene, 3-(3,5-dibromophenyl)propylene, methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino.

Optionally, the tumor is leukemia, lung cancer, malignant lymphoma, breast cancer, ovarian cancer, soft tissue sarcoma, osteosarcoma, rhabdomyosarcoma, Ewing sarcoma, blastoma, neuroblastoma, bladder cancer, thyroid cancer, prostate cancer, head and neck cancer, nasopharyngeal carcinoma, esophageal cancer, testicular cancer, stomach cancer, liver cancer, pancreatic cancer, cervical cancer, endometrial cancer, melanoma, or colorectal cancer.

In yet another aspect, the present disclosure provides a pharmaceutical composition comprising the above-mentioned Pt(IV) complex.

In another aspect, the present disclosure also provides the use of the above-mentioned Pt(IV) complex in the manufacture of a medicament for treating a tumor by radiation activation. Optionally, the radiation is from radiotherapy.

In yet another aspect, the present disclosure also provides a method for treating a tumor, which includes: administering the above-mentioned Pt(IV) complex to a subject, and irradiating the subject.

Optionally, the radiation is from radiotherapy.

Optionally, the radiotherapy is performed 0.5-6 h after the administration of the Pt(IV) complex.

In one embodiment, the radiation dose is less than 60 Gy.

Optionally, the tumor is leukemia, lung cancer, malignant lymphoma, breast cancer, ovarian cancer, soft tissue sarcoma, osteosarcoma, rhabdomyosarcoma, Ewing sarcoma, blastoma, neuroblastoma, bladder cancer, thyroid cancer, prostate cancer, head and neck cancer, nasopharyngeal carcinoma, esophageal cancer, testicular cancer, stomach cancer, liver cancer, pancreatic cancer, cervical cancer, endometrial cancer, melanoma, or colorectal cancer.

In yet another aspect, the present disclosure provides a kit comprising: the above-mentioned Pt(IV) complex or the above-mentioned pharmaceutical composition comprising the Pt(IV) complex, and description, indicating that the administration is followed by radiation therapy to treat a tumor.

BRIEF DESCRIPTION OF THE DRAWINGS

In order to illustrate the technical solutions of the examples of the present disclosure more clearly, the drawings of the examples will be briefly introduced below. Apparently, the drawings in the following description only relate to some examples of the present disclosure, rather than limiting the present disclosure.

DETAILED DESCRIPTION OF THE INVENTION

Figure 1:
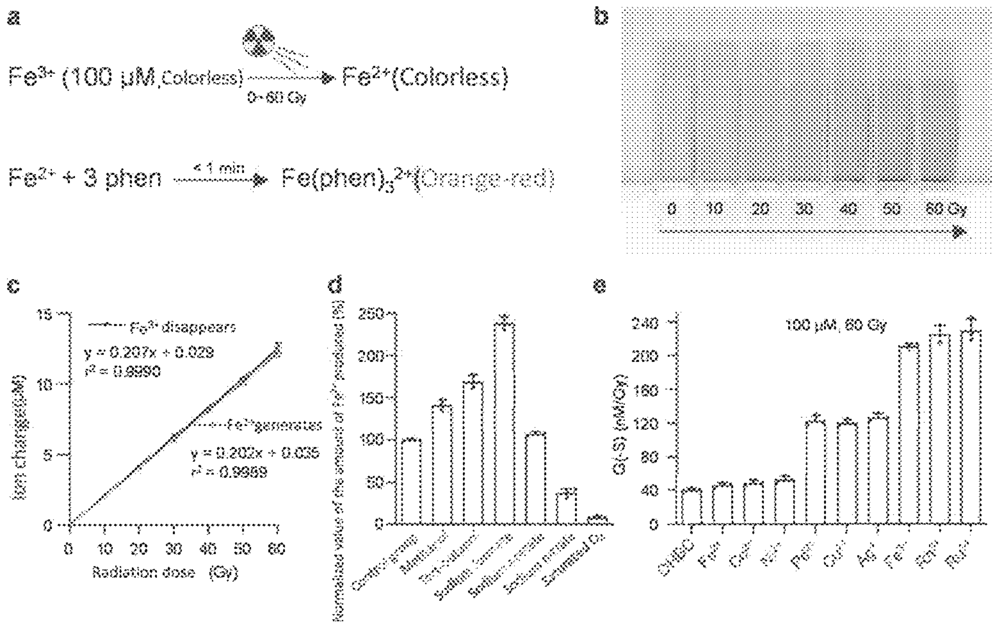
FIG. 1 depicts the broad-spectrum of radiation reduction of metal ions.

In order to make the purpose, technical solutions and advantages of the examples of the present disclosure clearer, the technical solutions of the examples of the present disclosure will be clearly and completely described below in conjunction with the drawings of the examples of the present disclosure. Apparently, the described examples are a part of the examples of the present disclosure, not all of the examples of the present disclosure. Based on the described examples of the present disclosure, all other examples obtained by those of ordinary skill in the art without creative effort shall fall within the protection scope of the present invention.

The present disclosure may be embodied in other specific forms without departing from essential attributes of the present disclosure. It should be understood that any and all embodiments of the present disclosure can be combined with technical features in any other embodiment or multiple other embodiments to obtain additional embodiments under the premise of no conflict. Additional embodiments resulting from such combinations are also included by the present disclosure.

All publications and patents mentioned in this disclosure are hereby incorporated by reference into this disclosure in their entirety. If usage or terminology used in any publications and patents incorporated by reference conflicts with usage or terminology used in the present disclosure, the usage and terminology in the present disclosure shall control.

The section headings used herein are for the purpose of organizing the article only and should not be construed as limitations on the subject matter described.

Unless defined otherwise, all technical and scientific terms used herein have their ordinary meanings in the art to which the claimed subject matter belongs. In the event that more than one definition exists for a term, the definition herein controls.

Except in the working examples or where otherwise indicated, all numbers expressing amounts of material, reaction conditions, duration, and quantitative properties of materials, etc. stated in the specification and claims are to be understood as being modified by the term "about" in all instances. It should also be understood that any numerical range recited herein is intended to include any combination of all subranges within that range and the respective endpoints of that range or subrange, for example, an alkyl group having 1 to 20 carbon atoms ($C_{1-20}$ alkyl) includes an alkyl group having 1, 2, 3, 4, 5, 6, 7, 8, 9, 10, 11, 12, 13, 14, 15, 16, 17, 18, 19 or 20 carbon atoms, and also includes an alkyl group having a subrange of carbon atoms of 1-4, 1-6, 1-10, 2-4, or 2-10.

The description of the present disclosure should be construed in accordance with the laws and principles of chemical bonding. In some cases it may be possible to remove a hydrogen atom in order to accommodate a substituent at a given position.

The words "comprising", "including" or "containing" and similar words used in the present disclosure mean that an element appearing before the words covers elements listed after the words and equivalents thereof, and does not exclude any unrecited element. The term "comprising" or "including (containing)" used herein can be open, semi-closed and closed. In other words, the term also includes "consisting essentially of" or "consisting of".

It should be understood that a singular form (e.g., "a" or "an") as used in this disclosure may include plural referents unless otherwise specified.

Unless otherwise indicated, this disclosure employs standard nomenclature and standard laboratory procedures and techniques of analytical chemistry, synthetic organic chemistry, and coordination chemistry. Unless otherwise stated, the present disclosure adopts traditional methods of mass spectrometry and elemental analysis, and the steps and conditions can refer to the conventional operation steps and conditions in the art.

The reagents and starting materials used in the present disclosure are commercially available or can be prepared by conventional chemical synthesis methods.

The term "optional" used herein to describe a situation means that the situation may or may not occur. For example, being optionally fused to a ring means that it is fused to or not fused to a ring. For example, the term "optionally substituted" as used herein refers to being unsubstituted or having at least one non-hydrogen substituent that does not destroy the desired property possessed by the unsubstituted analog.

In the present disclosure, unless otherwise specified, the number of "substitution" can be one or more. When the number of "substitution" is more than one, it can be 2, 3 or 4. Moreover, when the number of the "substitution" is more than one, the "substitution" may be the same or different.

In the present disclosure, the position of "substitution" can be arbitrary unless otherwise specified.

The term "axial ligands" as used herein refers to the two axial ligands in the $d^2sp^3$ hexa-coordinated structure of tetravalent platinum, which are released from a complex after the complex is reduced by irradiation.

The term "lateral ligands" as used herein refers to the four lateral ligands in the $d^2sp^3$ hexa-coordinated structure of tetravalent platinum, which can still be coordinated with a divalent platinum ion after the complex is reduced by irradiation.

As used herein, the term "neutral ligand" or "anionic ligand" refers to a ligand capable of being coordinated with platinum, wherein the ligand is uncharged or negatively charged as a whole, but may locally have a cation such as triphenylphosphonium or ammonium.

In the context of this application, unless specifically stated to the contrary, the term "treatment" may also include prophylaxis.

The term "subject" or "patient" in this application includes humans and mammals.

As used herein, the term "$C_1$-$C_{20}$alkyl" refers to a straight or branched alkane chain containing 1 to 20 carbon atoms. For example, representative examples of $C_1$-$C_6$ alkyl include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentyl ($C_5$), neopentyl ($C_5$), 3-methyl-2-butanyl ($C_5$), tert-amyl ($C_5$), and n-hexyl ($C_6$), etc. The term "lower alkyl" refers to a straight or branched chain alkyl having 1 to 4 carbon atoms. "Substituted alkyl" refers to an alkyl group substituted with one or more substituents, preferably 1 to 4 substituents, at any available point of attachment. The term "haloalkyl" refers to an alkyl group having one or more halogen substituents, including but is not limited to groups such as $-CH_2Br$, $-CH_2I$, $-CH_2Cl$, $-CH_2F$, $-CHF_2$, $-CF_3$, and the like.

The term "alkylene" as used herein refers to a divalent hydrocarbon group as described above for "alkyl" but having two points of attachment. For example, methylene is a $-CH_2-$ group, and ethylene is a $-CH_2-CH_2-$ group.

The term "alkoxy" or "alkylthio" as used herein refers to an alkyl group as described above linked via an oxygen bond ($-O-$) or a sulfur bond ($-S-$), respectively. The term "substituted alkoxy" or "substituted alkylthio" refers to a substituted alkyl group linked via an oxygen or sulfur bond, respectively. "Lower alkoxy" is the group $-OR$, wherein R is lower alkyl (alkyl containing 1 to 4 carbon atoms).

The term "halogen" as used herein refers to fluorine, chlorine, iodine or bromine.

The radiation sources of the present disclosure may be alpha, beta, gamma rays produced by the decay of radionuclides. X-rays, gamma rays, energetic electrons, protons, heavy ions produced by external radiation sources, and alpha particles produced by boron neutron capture therapy (BNCT), and other possible external or internal sources of radiation are also applicable to the present disclosure.

The high-energy rays used in radiotherapy have high spatial and temporal resolution, and high tissue penetration ability, and at the same time are highly clinically relevant. Using high-energy rays in radiotherapy to activate prodrug molecules and carry out chemical reactions in vivo has both basic research value and clinical application value.

The chemical reaction activated by high-energy rays involves the radiolysis of water by the rays to produce a large number of reactive species. The reactive species are then reacted with a target substrate. In the products of water radiolysis, the compounds with the highest yields are hydroxyl radicals and hydrated electrons.

A living body is generally a reducing environment, and a large number of substances such as glutathione and vitamin C can quench hydroxyl radicals and increase the production of hydrated electrons. As such, using hydrated electrons to carry out chemical reactions will be a big breakthrough in chemistry in vivo.

High-energy rays (such as X-rays and γ-rays) can be used as external stimuli to reduce tetravalent platinum complexes to obtain divalent platinum complexes. Due to the high penetrating power of the radiation, as well as the high spatio-temporal resolution of the radiation, the prodrug can be converted into the divalent platinum complex very efficiently by radiotherapy equipment. For example, since radiation-induced chemical reactions can be controlled in space and time. X-ray irradiation as an external trigger to activate prodrugs can precisely control the area, time, and dose of prodrugs converted to their active forms.

The present disclosure utilizes the properties of radiation to instantly and efficiently reduce metal complexes, so as to realize the release of Pt(II) drugs from Pt(IV) prodrugs, and achieve the purpose of controlled release of chemotherapy drugs. Therefore, the release of Pt(II) drugs such as Oxaliplatin by radiation reduction of less toxic Pt(IV) prodrugs can effectively inhibit various Oxaliplatin-sensitive cell lines. In HCT116 tumor-bearing mice, this strategy resulted in almost complete tumor regression. This reduction is mediated by hydrated electrons ($e_{aq}^-$) generated by water radiolysis, and adapted to the hypoxic reducing tumor microenvironment. Therefore, the strategy of using radiotherapy to activate prodrugs to release chemotherapeutic drugs has certain potential clinical value.

Radiotherapy is required in more than 50% of cases in cancer treatment. Modern radiotherapy techniques can precisely irradiate tumors and deliver high doses of radiation locally.

Cancer responses to radiation can be described by radiosensitivity. Highly radiosensitive cancer cells (leukemias, most lymphomas, and germ cell tumors) are rapidly killed by moderate doses of radiation. Moderately radiosensitive cancer cells (most epithelial cancers) require higher doses of radiation (60-70 Gy) to be completely killed. Some cancers (renal cell carcinoma and melanoma) are markedly radiation resistant and require much higher doses than those are clinically safe to be cured. Many common moderately radioreactive tumors typically receive radiation therapy if they are in the early stages. Metastatic cancer usually cannot be cured by radiation therapy because it is not possible to irradiate the entire body.

Radiation therapy itself is painless. Many low-dose palliative treatments (e.g., radiation therapy for bone metastases) cause little or no side effects. Higher doses can cause different side effects, including acute side effects during treatment, side effects months or years after treatment (long-term side effects), or side effects after retreatment (cumulative side effects). The nature, severity, and duration of side effects depend on the organ receiving radiation, radiation type, dose, times, concurrent chemotherapy, and patient. Side effects are dose-dependent; for example, higher doses of head and neck radiation may induce cardiovascular complications, thyroid dysfunction, and pituitary axis dysfunction. Modern radiation therapy is designed to minimize side effects and to help patients understand and deal with unavoidable side effects.

Radiation therapy uses photons or charged particles to damage the DNA of cancer cells. The atoms that make up DNA strands are directly or indirectly ionized. By ionizing water, indirect ionization forms free radicals, which then damage DNA Cells have mechanisms to repair DNA damage. Breaks in double-stranded DNA are more difficult to be repaired and can lead to significant chromosomal abnormalities and gene deletions. Targeting double-strand break can increase the likelihood of cells undergoing cell death. In the 1950s, experiments by Gray et al. showed that three times higher radiation doses were required to kill hypoxic cells compared to normoxic cells. Due to the limited tolerance of normal tissues to radiation, it is generally not possible to increase the radiation dose to compensate for tumor hypoxia. After radiotherapy, hypoxic tumor cells may persist and then divide, leading to tumor persistence and the development of a more aggressive tumor phenotype.

Radiotherapy is not conducive to DNA damage caused by oxygen-fixed radiation because the clinical radiation dose is limited (generally less than 60 Gy), and on the other hand, hypoxic tumors are often resistant to radiotherapy. Therefore, radiotherapy often needs to be combined with chemotherapy drugs to improve the cure rate of tumors. However, most clinically approved anticancer drugs have a narrow therapeutic window and high systemic toxicity, and prodrug strategies often need to be introduced to further increase the dosage and reduce toxicity. The dose of a prodrug can exceed 50 times of the normal dose, and a prodrug can overcome the tumor's resistance to chemotherapy drugs to a certain extent. However, due to the limited activation efficiency of prodrugs and the lack of tumor selectivity, prodrug strategies are difficult to be achieved clinically. If radiotherapy is used as a precise exogenous stimulus to highly selectively activate the original drug at the tumor site, the above problems would be solved. However, at present, no in vivo radiation-induced lysis chemistry has yet been established in vivo, and only partial work in the past three decades has achieved this strategy at the test-tube or cellular level. However, radiation-induced activation of chemotherapeutic agents is difficult to have clinical impact without establishing radiation-activated chemical reactions in vivo.

The radiochemical change of molecules is the material basis for the study of all radiochemical effects. There are two main types of radiochemical effects: direct effects in which ionizing radiation causes direct chemical changes in target molecules, and indirect effects in which radiation deposits on environmental molecules and then causes indirect chemical interactions in target molecules. Direct and indirect effects exist simultaneously, but indirect effect dominates in vivo. Because the tissue comprises 70-80% water, various active substances are mainly produced through the radiolysis of water (Scheme 1a), wherein substances with the highest yields are hydroxyl radicals (OH) and hydrated electrons (ea). The radiolysis of water is completed within $10^{-4}$ seconds, so the radiation-induced reaction tends to occur instantaneously, and thus has strong controllability. OH-induced cleavage chemistry reaction and related fluorescent probes have been successfully used in bioimaging, but the rapid quenching of OH by the reducing tumor microenvironment hinders its development in living systems. However, the yield of radiation-induced ea, another major product of water radiolysis, increases in reducing environments. Therefore, here we explore the feasibility of locally generating e by precise radiotherapy to mediate chemical cleavage reactions (Scheme 1b), and the use of radiation as a chemical tool to release target molecules in a highly tumor-selective manner (Scheme Ic).

Scheme1a $$H_2O \xrightarrow[\text{Radiation}]{\text{Ionization}} \underset{2.63}{e^-_{aq}},\ H^+,\ \underset{0.55}{H\bullet},\ \underset{2.72}{\bullet OH},\ \underset{0.45}{H_2},\ \underset{0.68}{H_2O_2}$$

Scheme 1b(M is Fe, Co, Ni, Cu, Ru, Rh, Pd, Ag, etc.)

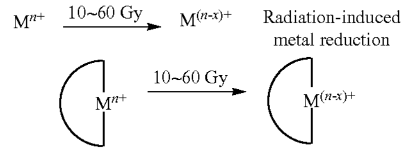

Scheme 1c

Scheme 1. Radiation-induced controlled release of metal complexes in tumors.

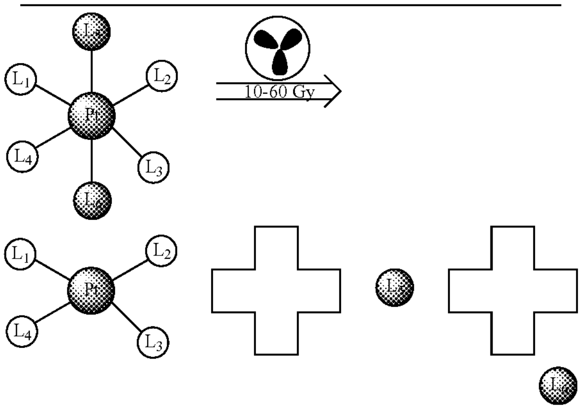

a, Radiolysis of water by ionizing radiation. The G value of hydrated electrons is 2.63 (G value refers to the number of molecules formed by absorbing 100 eV energy in the system). b, Radiation-generated hydrated electrons can reduce metal ions and metal complexes. c, Pt(IV) complexes can be reduced by irradiation to release Pt(II) anticancer drugs.

The inventors achieved radiation-induced metal reduction in vivo through research, thereby constructing a new in vivo cleavage chemistry. By applying this strategy to the activation of Pt(IV) prodrugs, radiotherapy becomes an exogenous stimulus that triggers drug release, thereby achieving the release of chemotherapeutic drugs at the tumor site under the guidance of precise radiotherapy. In addition, this strategy is also helpful to solve the problem of radiotherapy resistance in hypoxic tumors, and instead can improve the drug release efficiency under hypoxic conditions. The direct metal reduction of $e_{aq}^-$ induced by radiation can also be extended to other metals or biological complexes (such as metalloproteins), providing an efficient tool for the mechanistic dissection of complex biological processes.

One aspect of the present disclosure provides a Pt(IV) complex of formula (I), which is activated by irradiation as a prodrug to treat a tumor, (I)

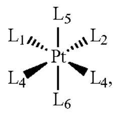

wherein $L_1$ to $L_6$ are ligands of platinum: the complex can release $L_5$ and $L_6$ after irradiation to obtain a Pt(II) complex of formula (II).

(II)

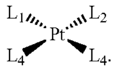

The Pt(IV) complex of formula (I) of the present disclosure releases axial ligands $L_5$ and $L_6$ through reduction to obtain the Pt(II) complex of formula (II). The Pt(IV) complex of formula (I) is developed on the basis of the Pt(II) complex, and can be regarded as a prodrug of the Pt(II) complex of formula (II). According to the corresponding relationship between the above-mentioned formula I and formula II, the lateral ligands $L_1$ to $L_4$ of the Pt(IV) complex of formula (I) can be determined from the ligands $L_1$ to $L_4$ of the Pt(II) complex of formula (II).

The lateral ligands of the Pt(IV) complex of formula (I) can be in a cis or trans configuration. In one embodiment, the lateral ligands of the Pt(IV) complex of formula (I) are in a cis configuration.

In one embodiment, the Pt(II) complex of formula (II) is a cis-configured Pt(II) complex.

The Pt(II) complex of formula (II) may be a divalent platinum complex known to have anticancer activity. In one embodiment, the Pt(II) complex of formula (II) is a divalent platinum complex that has been marketed or has entered clinical practice, such as Cisplatin, Carboplatin, Nedaplatin, Oxaliplatin, Lobaplatin, Heptaplatin, Cycloplatin, Miboplatin, Enloplatin, Sebriplatin, Spiroplatin, Zeniplatin, TRK-710, Aroplatin, bis(isopropylamine)platinum(II) dichloride, or bis(cyclopentylamine)platinum(II) dichloride.

In a preferred embodiment, the Pt(II) complex of formula (II) is Cisplatin, Carboplatin, Nedaplatin, Oxaliplatin, Lobaplatin, or Heptaplatin.

$L_5$ and $L_6$ are respectively the negative monovalent ligands of Pt(IV), which can be released from the Pt(IV) complex of formula (I) under irradiation. $L_5$ and $L_6$ can be the same or different.

In one embodiment, $L_5$ and $L_6$ are respectively $^-$O—C(O)—R, wherein R is selected from optionally substituted $C_{1-20}$ alkyl, optionally substituted $C_{1-20}$ alkyloxy or optionally substituted amino, wherein the substituent is selected from $C_{1-18}$ alkyl, carboxyl, hydroxyl, halogen, mercapto, amino, di-$C_{1-3}$ alkylamino, carbonyl, phenyl, halophenyl, $C_{1-6}$ alkyl-substituted phenyl, a maleimide group, and triphenylphosphonium. "Optionally substituted" here means that the $C_{1-20}$ alkyl or amino group may be substituted by a substituent or unsubstituted. Unsubstituted $C_{1-20}$ alkyl includes methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, and eicosyl. Those skilled in the art will rationally select substituents according to the stability of a chemical structure.

In one embodiment, $L_5$ and $L_6$ are respectively $^-$O—C(O)—R, wherein each R is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, eicosyl, carboxymethylene, 2-carboxyethylene, 3-carboxypropylene, 4-carboxybutylene, 5-carboxypentylene, 6-carboxyhexylene, (dimethylamino)methylene, 2-(dimethylamino)ethylene, 3-(dimethylamino)propylene, 4-(dimethylamino)butylene, 5-(dimethylamino)pentylene, 6-(dimethylamino)hexylene, 5-maleimidopentylene, 6-maleimidohexylene, 7-maleimidoheptylene, 8-maleimidooctylene, 3-(4-iodophenyl)propylene, 3-(3-iodophenyl)propylene, 3-(3,5-diiodophenyl)propylene, 3-(4-bromophenyl)propylene, 3-(3-bromophenyl)propylene, 3-(3,5-dibromophenyl)propylene, methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino.

For example, platinum(IV) complexes are Cisplatin-based prodrugs: compounds 1-22.

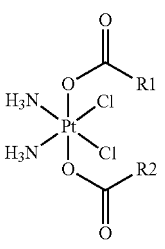

wherein:

$R_1$ = 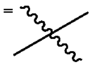 $R_2$ = 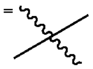 Compound 1

-continued
$R_1$ = 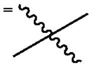 $R_2$ = 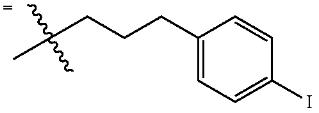 Compound 2
$R_1$ = 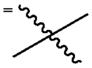 $R_2$ = 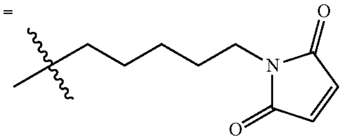 Compound 3
$R_1$ = 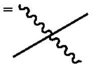 $R_2$ = 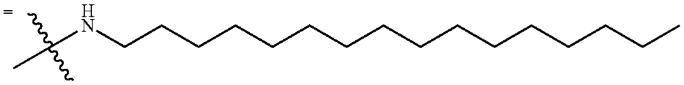 Compound 4
$R_1$ = 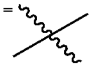 $R_2$ = 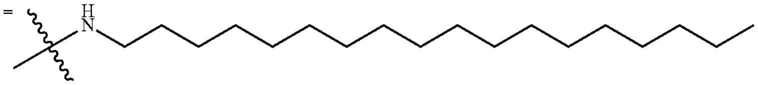 Compound 5
$R_1$ = 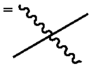 $R_2$ = 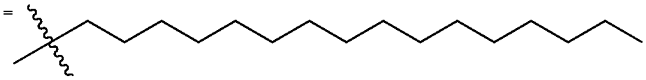 Compound 6
$R_1$ = 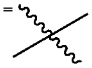 $R_2$ = 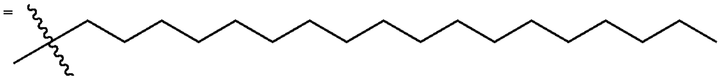 Compound 7
$R_1$ = 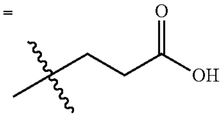 $R_2$ = 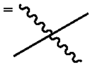 Compound 8
$R_1$ = 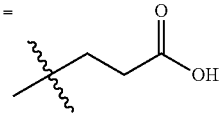 $R_2$ = 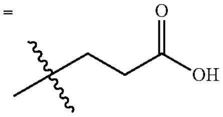 Compound 9
$R_1$ = 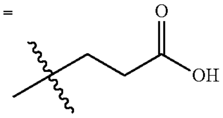 $R_2$ = 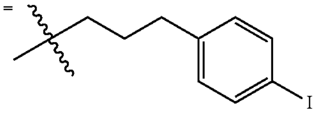 Compound 10
$R_1$ = 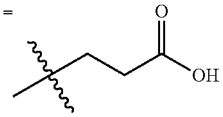 $R_2$ = 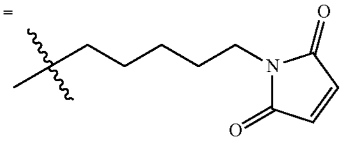 Compound 11
$R_1$ = 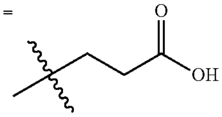 $R_2$ = 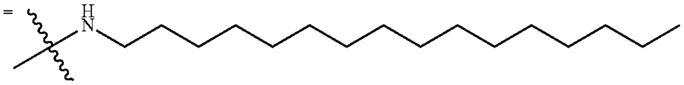 Compound 12
$R_1$ = 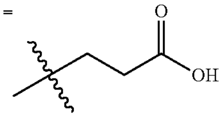 $R_2$ = 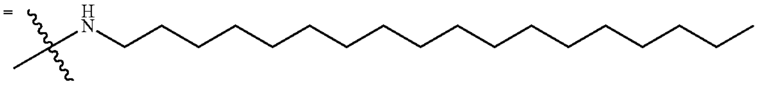 Compound 13
$R_1$ = 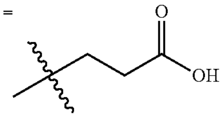 $R_2$ = 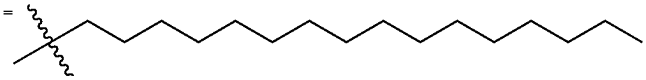 Compound 14

-continued
| | | |
|---|---|---|
| $R_1$ = 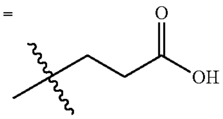 | $R_2$ = 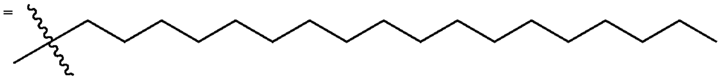 | Compound 15 |
| $R_1$ = 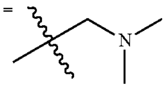 | $R_2$ = 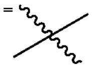 | Compound 16 |
| $R_1$ = 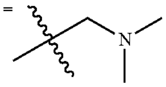 | $R_2$ = 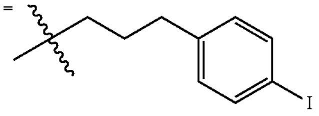 | Compound 17 |
| $R_1$ = 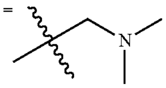 | $R_2$ = 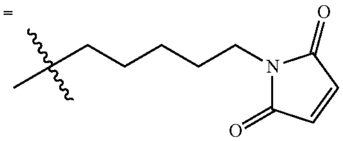 | Compound 18 |
| $R_1$ = 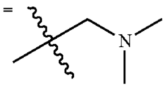 | $R_2$ = 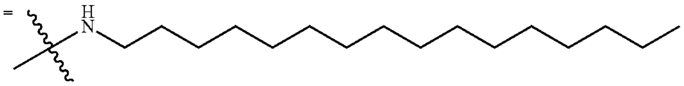 | Compound 19 |
| $R_1$ = 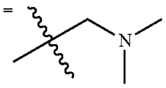 | $R_2$ = 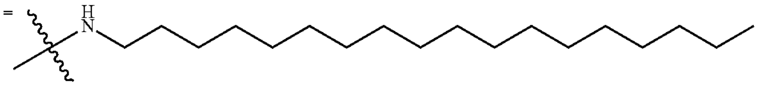 | Compound 20 |
| $R_1$ = 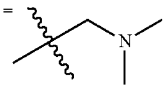 | $R_2$ = 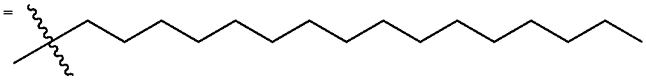 | Compound 21 |
| $R_1$ = 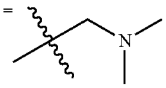 | $R_2$ = 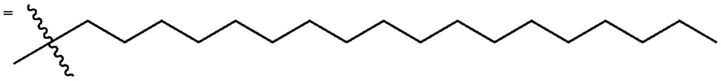 | Compound 22 |
For example, platinum(IV) complexes are Carboplatin-based prodrugs: compound 23-44.
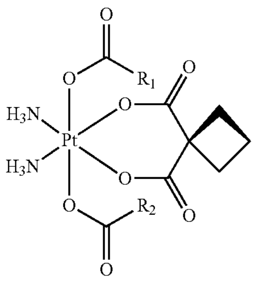
wherein:
| | | |
|---|---|---|
| $R_1$ = 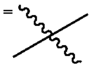 | $R_2$ = 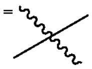 | Compound 23 |

-continued
$R_1$ = 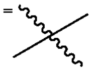 $R_2$ = 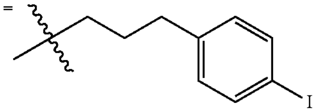 Compound 24
$R_1$ = 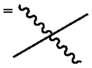 $R_2$ = 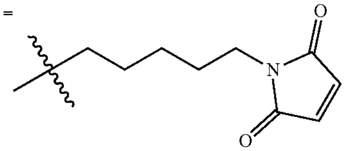 Compound 25
$R_1$ = 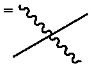 $R_2$ = 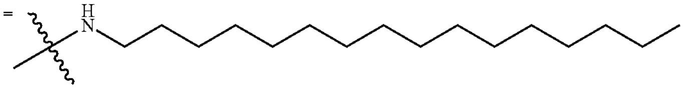 Compound 26
$R_1$ = 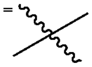 $R_2$ = 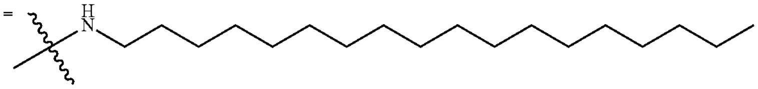 Compound 27
$R_1$ = 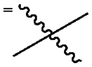 $R_2$ = 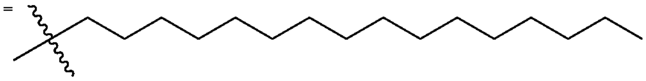 Compound 28
$R_1$ = 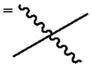 $R_2$ = 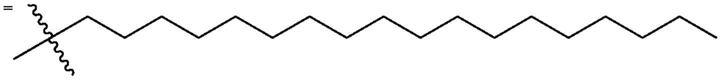 Compound 29
$R_1$ = 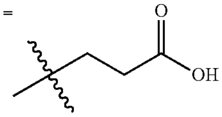 $R_2$ = 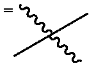 Compound 30
$R_1$ = 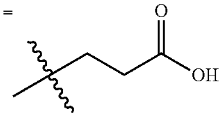 $R_2$ = 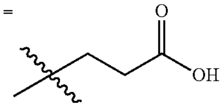 Compound 31
$R_1$ = 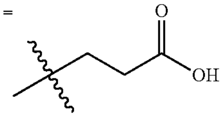 $R_2$ = 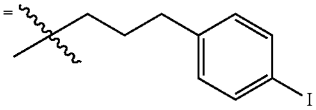 Compound 32
$R_1$ = 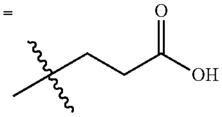 $R_2$ = 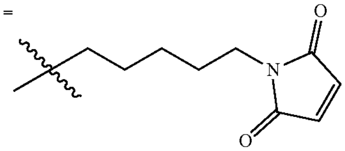 Compound 33
$R_1$ = 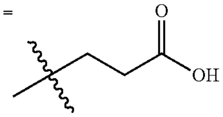 $R_2$ = 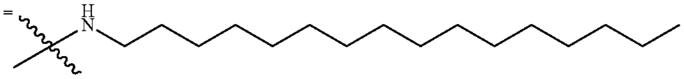 Compound 34
$R_1$ = 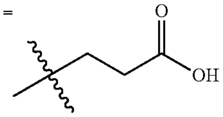 $R_2$ = 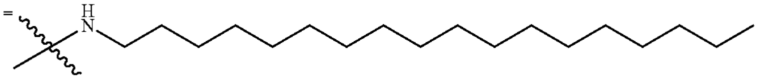 Compound 35

-continued
| | | |
|---|---|---|
| $R_1$ = 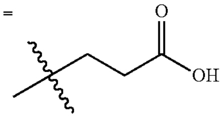 | $R_2$ = 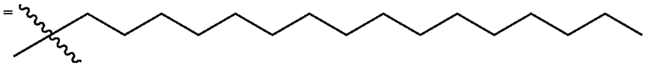 | Compound 36 |
| $R_1$ = 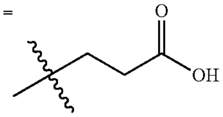 | $R_2$ = 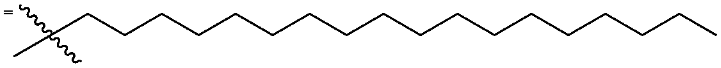 | Compound 37 |
| $R_1$ = 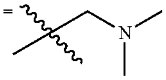 | $R_2$ = 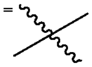 | Compound 38 |
| $R_1$ = 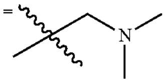 | $R_2$ = 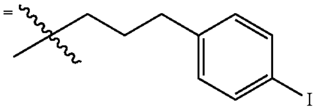 | Compound 39 |
| $R_1$ = 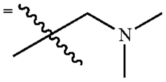 | $R_2$ = 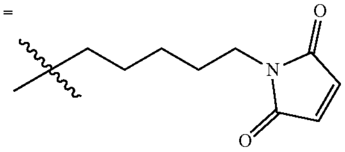 | Compound 40 |
| $R_1$ = 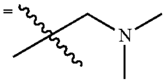 | $R_2$ = 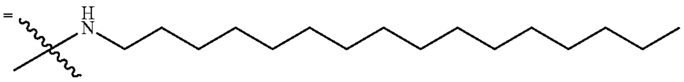 | Compound 41 |
| $R_1$ = 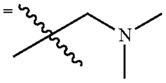 | $R_2$ = 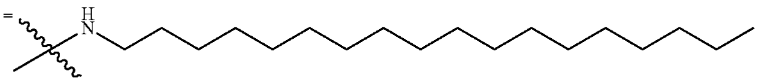 | Compound 42 |
| $R_1$ = 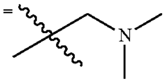 | $R_2$ = 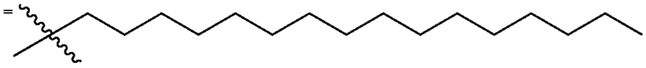 | Compound 43 |
| $R_1$ = 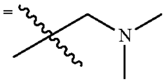 | $R_2$ = 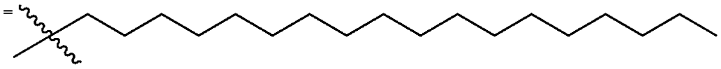 | Compound 44 |
For example, platinum(IV) complexes are Oxaliplatin-based prodrugs: compound 45-06.
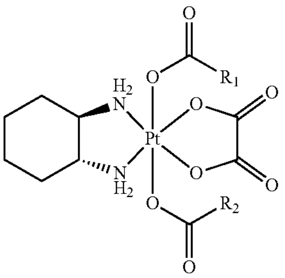
wherein:
| | | |
|---|---|---|
| $R_1$ = 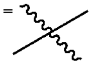 | $R_2$ = 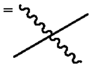 | Compound 45 |

-continued
$R_1$ = 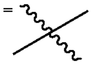 $R_2$ = 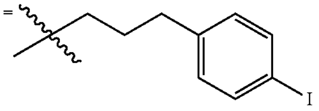 Compound 46
$R_1$ = 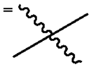 $R_2$ = 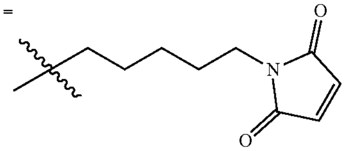 Compound 47
$R_1$ = 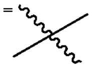 $R_2$ = 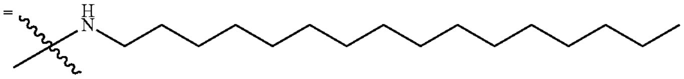 Compound 48
$R_1$ = 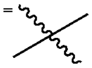 $R_2$ = 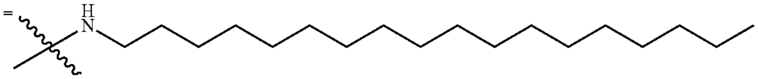 Compound 49
$R_1$ = 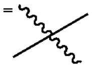 $R_2$ = 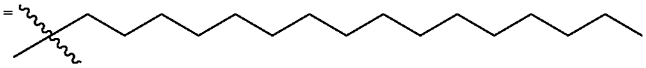 Compound 50
$R_1$ = 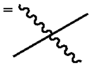 $R_2$ = 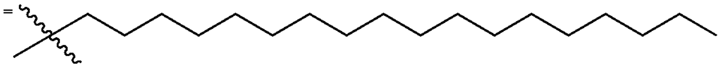 Compound 51
$R_1$ = 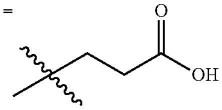 $R_2$ = 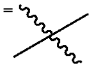 Compound 52
$R_1$ = 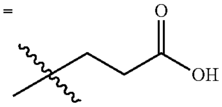 $R_2$ = 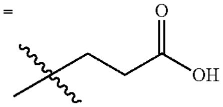 Compound 53
$R_1$ = 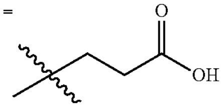 $R_2$ = 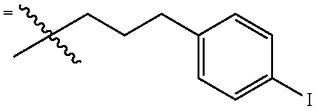 Compound 54
$R_1$ = 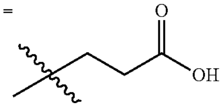 $R_2$ = 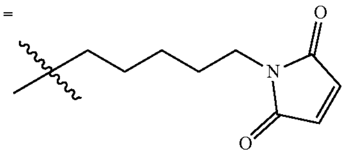 Compound 55
$R_1$ = 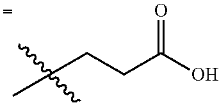 $R_2$ = 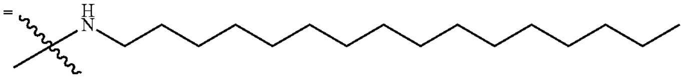 Compound 56
$R_1$ = 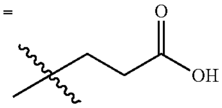 $R_2$ = 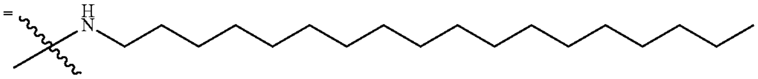 Compound 57

-continued

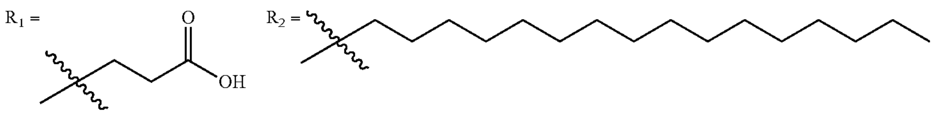
Compound 58

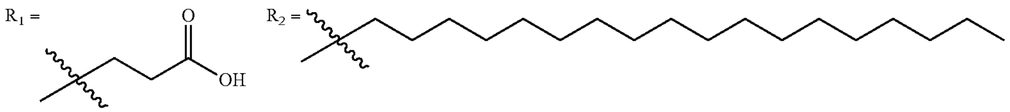
Compound 59

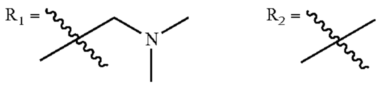
Compound 60

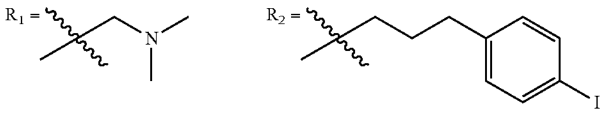
Compound 61

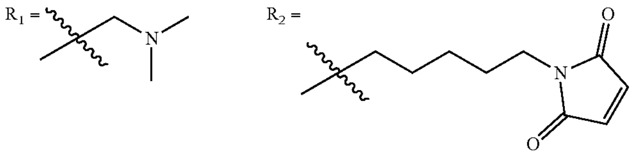
Compound 62

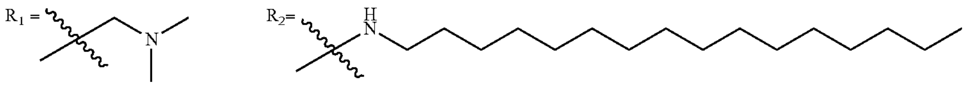
Compound 63

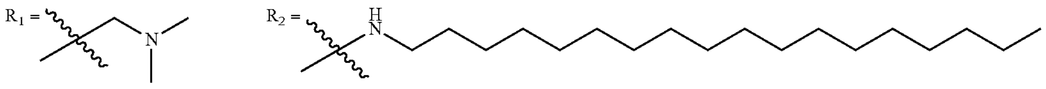
Compound 64

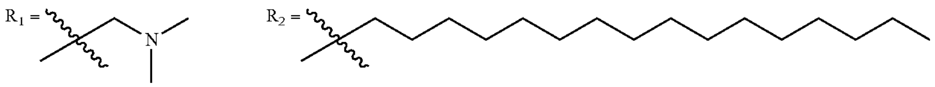
Compound 65

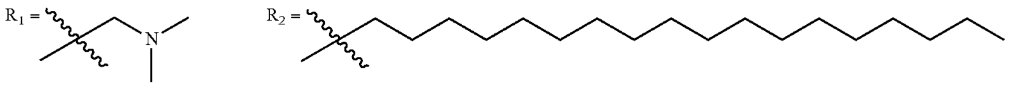
Compound 66

The Platinum(IV) complex can be obtained by oxidizing divalent platinum complex of formula (II) with an oxidizing agent such as hydrogen peroxide to obtain a platinum(IV) dihydroxy complex, and replacing the two hydroxyl groups on the platinum(IV) dihydroxy complex with carboxylate groups under the action of an acylating agent such as an anhydride.

For example, platinum(IV) complexes can be prepared by the following scheme:

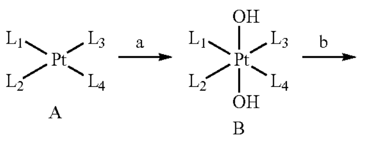

-continued

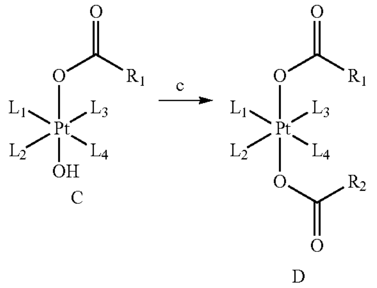

The corresponding Pt(II) drug A (12.6 mmol, 1.0 equiv) was mixed with 12 mL of $H_2O_2$, diluted with 15 mL of $H_2O$ and stirred at 50° C. for 5 h. After the Pt(II) drug was completely consumed, the product was collected in a centrifuge tube at room temperature, and washed respectively with water, ethanol, and ether. The precipitate was lyophilized to obtain a white powder as compound B.

Compound B (1.0 equivalent) was mixed with the corresponding anhydride (such as: succinic anhydride, acetic anhydride. N,N-dimethylglycine anhydride)(1.0 equivalent), and dissolved in 4 mL of anhydrous DMF, and then stirred for 1 hour to obtain unpurified compound C.

Compound D (urethane bond, i.e., $R_2$ represents an amino compound):

A 2 mL solution of the corresponding isocyanate in anhydrous DMF was added to the above reaction solution. After reacting overnight, the solvent was removed under reduced pressure at 65° C. To an oily residue was added 2 mL of diethyl ether. The mixture was sonicated for 1 min and then centrifuged. The solid was further washed with 4 mL of DCM and 2 mL of diethyl ether. The washed solid was placed under vacuum overnight to obtain compound D.

Compound D (ester bond, i.e., $R_2$ represents an alkyl compound):

Compound C was precipitated with diethyl ether and lyophilized to obtain a white powder. Compound C (1.0 equivalent) and corresponding carboxylic acid (2.0 equivalent) were dissolved in 5 mL of DMF, and a condensing agent TBTU (2.0 equivalent) was added. The mixture was heated to 50° C., and reacted in the dark overnight. After evaporating the solvent under reduced pressure, the precipitate was washed with water, and then lyophilized with a lyophilizer to obtain compound D.

It is believed that the tetravalent platinum complexes of the present disclosure treat tumors primarily by being reduced to divalent platinum in vivo. Although the administration of tetravalent platinum complexes (oral, intravenous and body cavity administration, etc.) will cause the drug to spread throughout most of the organs and tissues of the body along with the blood circulation, the tetravalent platinum complexes will be reduced to divalent platinum by the cells themselves at different levels in various organs and tissues. However, with subsequent radiotherapy, the tumor can be precisely irradiated, delivering high doses of radiation locally, thereby locally increasing the reduction of tetravalent platinum to bivalent platinum.

The tetravalent platinum complex prodrug of the present disclosure can be used to treat leukemia, lung cancer, malignant lymphoma, breast cancer, ovarian cancer, soft tissue sarcoma, osteosarcoma, rhabdomyosarcoma, Ewing sarcoma, blastoma, neuroblastoma, bladder cancer, thyroid cancer, prostate cancer, head and neck cancer, nasopharyngeal carcinoma, esophageal cancer, testicular cancer, stomach cancer, liver cancer, pancreatic cancer, cervical cancer, endometrial cancer, melanoma, or colorectal cancer.

Another aspect of the present disclosure provides a pharmaceutical composition comprising the above-mentioned Pt(IV) complex and a pharmaceutically acceptable adjuvant.

The term "pharmaceutically acceptable" in this application means that a compound or composition is chemically and/or toxicologically compatible with other ingredients making up the formulation and/or with the human or mammal in which it is used to prevent or treat a disease or condition.

The term "adjuvant" in this application refers to an excipient or vehicle used to administer a compound, including but not limited to diluents, disintegrants, precipitation inhibitors, surfactants, glidants, binders, lubricants, coating materials, etc. Adjuvants are generally described in "Remington's Pharmaceutical Sciences" by E. W. Martin. Examples of adjuvants include, but are not limited to, vegetable oils, cyclodextrins, aluminum monostearate, aluminum stearate, carboxymethylcellulose, sodium carboxymethylcellulose, crospovidone, glyceryl isostearate, glyceryl monostearate, hydroxyethyl cellulose, hydroxymethyl cellulose, hydroxvoctacosvl hydroxystearate, hydroxypropyl cellulose, hydroxypropylmethyl cellulose, lactose, lactose monohydrate, magnesium stearate, mannitol, and microcrystalline cellulose, etc.

At least one embodiment of the present disclosure provides a method of preparing a pharmaceutical composition, comprising mixing at least one Pt(IV) complex of the present disclosure with a pharmaceutically acceptable adjuvant.

The Pt(IV) complex of the present disclosure can be formulated into injections and powder injections, diluted with physiological saline or 5% glucose solution, and then administered by intravenous infusion.

Divalent platinum drugs are usually administered parenterally and are not suitable for oral administration. However, the Pt(IV) complex of the present disclosure can also be formulated into a pharmaceutical composition for oral administration.

For example, a pharmaceutical composition for oral administration comprises a suspension of the Pt(IV)complex in at least one pharmaceutically acceptable vegetable oil, animal oil, mineral oil, synthetic oil or semi-synthetic oil. In one embodiment, the pharmaceutical composition may be enclosed in hard gelatin or hydroxypropylmethyl cellulose capsules or in soft gelatin capsules, and the capsules contain 50 to 350 mg of the Pt(IV) complex.

For example, a pharmaceutical composition for oral administration may comprise a form of inclusion of cyclodextrin and the Pt(IV) complex, which is obtained by dissolving a Pt(IV) complex in an organic solvent such as acetone, then reacting it with a cyclodextrin such as a $C_{1-4}$ hydroxyalkyl-substituted D or γcyclodextrin, and then removing the solvent by low-pressure sublimation drying.

The present disclosure also provides the use of the above-mentioned Pt(IV) complex in the manufacture of a medicament for treating a tumor by radiation activation.

In yet another aspect, the present disclosure also provides a method for treating a tumor, which includes: administering the above-mentioned Pt(IV) complex to a subject, and irradiating the subject.

In one embodiment, the irradiation is from radiotherapy.

Radiation therapy includes: external beam radiation therapy (including conventional external beam radiation therapy; stereotactic radiation; 3D conformal radiation therapy; intensity-modulated radiation therapy), particle therapy, Auger therapy, contact X-rays, brachytherapy (particle interventional therapy), and radionuclide therapy.

The equipment that can be used includes: deep X-ray therapy machine, cobalt-60 therapy machine, medical electron linear accelerator, medical proton accelerator, medical heavy ion accelerator, and gamma knife, etc.

Please note that radiotherapy in this disclosure is different from concurrent chemoradiotherapy: concurrent chemoradiotherapy uses small doses of chemotherapy to increase tissue sensitivity to radiation; while the radiotherapy of the present disclosure is to promote the reduction of a prodrug into a divalent platinum drug by irradiation w % bile chemotherapy is performed. Please note that radiotherapy in this disclosure is also different from sequential chemoradiotherapy: sequential chemoradiotherapy is a group of chemotherapy followed by a group of radiation therapy or a group of radiation therapy followed by a group of chemotherapy; however, radiotherapy in the present disclosure is performed shortly after chemotherapy, for example, 0.5-6 hours later.

In one embodiment, the radiotherapy is performed 0.5-6 hours after administration of the Pt(IV) complex.

For example, the radiotherapy is carried out at 0.5, 1 h, 1.5 h, 2 h, 2.5 h, 3 h after administration of the Pt(IV) complex, and the radiotherapy is irradiated for 1-10 minutes (for example, 1, 2, 3, 4, 5 minutes).

For example, the radiotherapy equipment is a linear accelerator (such as Clinac iX of Varian Medical System), which generates X-rays with an energy of 6 MeV. The total local irradiation dose of a tumor is 4 Gy, and the dose rate is 2 Gy/min. The treatment regimen is as follows: the treatment is performed twice a week (drug+radiotherapy is one treatment), the radiotherapy is given 2 hours after the administration of the Pt(IV) complex, the radiotherapy time is about 2 minutes, and the interval is 2 days; the treatment needs to be repeated for a total of four weeks,

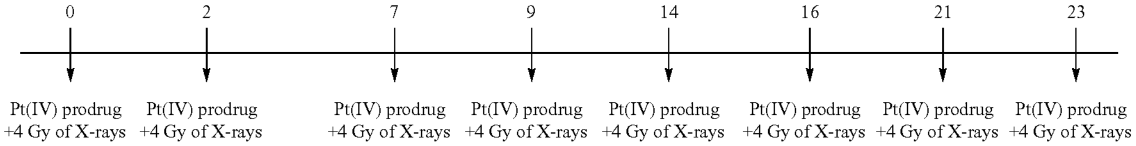

The Pt(IV) complex of the present disclosure combined with radiotherapy can achieve the treatment of hypoxic tumors that cannot be treated by conventional radiotherapy, such as pancreatic cancer and prostate cancer.

The radiotherapy scheme of the present disclosure can be carried out by conventional radiotherapy methods, and can also be carried out by using a lower dose than conventional radiotherapy methods. The side effects of radiotherapy can be reduced when the lower doses are used.

In one embodiment, the radiation dose is less than 60 Gy.

The Pt(IV) complex of the present disclosure can be used in combination with radiotherapy for the treatment of cancer, such as leukemia, lung cancer, malignant lymphoma, breast cancer, ovarian cancer, soft tissue sarcoma, osteosarcoma, rhabdomyosarcoma, Ewing sarcoma, blastoma, neuroblastoma, bladder cancer, thyroid cancer, prostate cancer, head and neck cancer, nasopharyngeal carcinoma, esophageal cancer, testicular cancer, stomach cancer, liver cancer, pancreatic cancer, cervical cancer, endometrial cancer, melanoma, or colorectal cancer.

In yet another aspect, the present disclosure provides a kit, which comprises the above-mentioned Pt(IV) complex or the above-mentioned pharmaceutical composition comprising the Pt(IV) complex, and also includes description, which indicates that radiotherapy is performed after administration to treat a tumor.

EXAMPLE

The starting materials for the examples are commercially available and/or can be prepared in a variety of ways well known to those skilled in the art of organic synthesis. Those skilled in the art of organic synthesis will appropriately select reaction conditions (including solvent, reaction atmosphere, reaction temperature, duration of test, and workup) in the synthetic methods described below. Those skilled in the art of organic synthesis will understand that the functional groups present on each part of the molecule should be compatible with the proposed reagents and reactions.

Reagents and Instruments

All chemical reagents were purchased from Energy Chemicals (China), J&K Scientific (China), Innochem (China) and Sinopharm (China) and were used as received without further purification. Solvents were distilled before use after dehydration with Na or $CaH_2$. Cell counting kit-8 (CCK-8) was purchased from Beyotime Institute of Biotechnology. Ultrapure water (18.2 MΩ/cm) used throughout the process was from a Milli-Q reference system (Millipore). Nuclear magnetic resonance (NMR) spectra were recorded on a Bruker AVANCE 400 MHz spectrometer. Ultra-performance liquid chromatography-mass spectrometry (UPLC-MS) was performed on an ACQUITY UPLC H-Class PLUS instrument equipped with a Waters PDA eλ detector and a Waters Acquity QDA mass spectrometer. Absorption spectra were measured by UV-1100 spectrophotometer. X-ray irradiation was generated by an X-ray generator (RS2000 Pro 225, 225 kV, 17.7 mA; Rad Source Technologies, Inc.). The total dose for a single test tube test was 0-60 Gy. and the dose rate was 5 Gv/min. The total dose for a cell test was 0~16 Gv, and the dose rate was 1.6 Gv/min. The implanted tumor was locally irradiated using a custom-made mouse mold. The local irradiation dose of the tumor was 4 Gy, and the dose rate was 1 Gy/min. The rest of the body was shielded with 5 mm thick lead. Gamma-ray irradiation was provided by a $^{60}Co$ source.

1. Synthesis and Characterization of Pt(IV) Complexes

The Pt(IV) complexes were prepared by the corresponding Pt(II) drugs as described above, and the platinum(IV) dihydroxy complexes were obtained after oxidation with hydrogen peroxide. Compounds 1 to 66 were prepared by reacting the two hydroxyl groups on the platinum(IV) dihydroxy complexes with the corresponding anhydrides. The products were characterized by mass spectrometry.

| | Theoretical mass-to-charge ratio | Mass spectrometry detection signal (positive charge peak after adding hydrogen ion) | Release efficiency |
|---|---|---|---|
| Compound 1 | 416.9822 | 418.03 | 83.2% |
| Compound 2 | 646.9414 | 648.05 | 85.7% |
| Compound 3 | 568.0455 | 569.04 | 80.3% |
| Compound 4 | 642.2278 | 643.32 | 79.5% |
| Compound 5 | 670.2591 | 671.38 | 73.9% |
| Compound 6 | 613.2013 | 614.34 | 81.4% |
| Compound 7 | 641.2326 | 642.38 | 80.8% |
| Compound 8 | 474.9877 | 476.03 | 75.5% |
| Compound 9 | 532.9931 | 534.22 | 75.6% |
| Compound 10 | 704.9469 | 705.99 | 76.7% |
| Compound 11 | 626.0510 | 627.17 | 73.9% |
| Compound 12 | 700.2333 | 701.37 | 77.4% |
| Compound 13 | 728.2646 | 729.48 | 82.7% |
| Compound 14 | 671.2068 | 672.55 | 73.6% |
| Compound 15 | 699.2381 | 700.40 | 77.8% |
| Compound 16 | 460.0244 | 461.04 | 71.9% |
| Compound 17 | 689.9836 | 690.13 | 79.6% |
| Compound 18 | 611.0877 | 612.31 | 73.5% |
| Compound 19 | 685.2700 | 686.32 | 78.5% |
| Compound 20 | 713.3013 | 714.57 | 83.7% |
| Compound 21 | 656.2435 | 657.61 | 77.5% |
| Compound 22 | 684.2748 | 685.39 | 76.7% |
| Compound 23 | 489.0711 | 490.32 | 72.5% |
| Compound 24 | 719.0303 | 720.14 | 71.9% |
| Compound 25 | 640.1344 | 641.09 | 68.5% |
| Compound 26 | 714.3167 | 715.87 | 69.4% |

-continued

| | Theoretical mass-to-charge ratio | Mass spectrometry detection signal (positive charge peak after adding hydrogen ion) | Release efficiency |
|---|---|---|---|
| Compound 27 | 742.3480 | 743.66 | 64.7% |
| Compound 28 | 685.2902 | 686.64 | 66.5% |
| Compound 29 | 713.3215 | 714.59 | 69.5% |
| Compound 30 | 547.0766 | 549.07 | 63.4% |
| Compound 31 | 605.0820 | 606.17 | 65.9% |
| Compound 32 | 777.0358 | 778.22 | 64.6% |
| Compound 33 | 698.1399 | 699.15 | 67.7% |
| Compound 34 | 772.3222 | 773.41 | 69.8% |
| Compound 35 | 800.3535 | 801.46 | 73.5% |
| Compound 36 | 743.2957 | 744.32 | 68.9% |
| Compound 37 | 771.3270 | 772.51 | 66.3% |
| Compound 38 | 532.1133 | 532.49 | 72.3% |
| Compound 39 | 762.0725 | 763.17 | 71.0% |
| Compound 40 | 683.1766 | 684.25 | 68.9% |
| Compound 41 | 757.3589 | 758.58 | 67.5% |
| Compound 42 | 785.3902 | 786.52 | 66.3% |
| Compound 43 | 728.3324 | 729.36 | 70.3% |
| Compound 44 | 756.3637 | 757.45 | 72.6% |
| Compound 45 | 515.0867 | 516.26 | 81.4% |
| Compound 46 | 745.0460 | 746.18 | 80.5% |
| Compound 47 | 666.1501 | 667.25 | 82.3% |
| Compound 48 | 740.3324 | 741.37 | 78.7% |
| Compound 49 | 768.3637 | 769.43 | 77.4% |
| Compound 50 | 711.3058 | 712.42 | 76.3% |
| Compound 51 | 739.3371 | 740.37 | 73.5% |
| Compound 52 | 573.0922 | 574.13 | 77.6% |
| Compound 53 | 631.0977 | 632.21 | 76.7% |
| Compound 54 | 803.0515 | 804.13 | 75.3% |
| Compound 55 | 724.1555 | 725.22 | 81.9% |
| Compound 56 | 798.3379 | 799.35 | 80.2% |
| Compound 57 | 826.3692 | 827.48 | 76.3% |
| Compound 58 | 769.3113 | 770.34 | 81.3% |
| Compound 59 | 797.3426 | 798.41 | 82.0% |
| Compound 60 | 558.1289 | 559.16 | 81.3% |
| Compound 61 | 788.0882 | 789.03 | 73.7% |
| Compound 62 | 709.1923 | 710.25 | 74.5% |
| Compound 63 | 783.3746 | 784.19 | 75.7% |
| Compound 64 | 811.4059 | 812.41 | 82.2% |
| Compound 65 | 754.3480 | 755.39 | 74.6% |
| Compound 66 | 782.3793 | 783.38 | 77.5% |

2. Analysis Method 2.1 Detection of Iron Ions and Complexes $Fe^{2+}/Fe^{3+}$ stock solution: 2.78 mg of $FeSO_4 \cdot 7H_2O$ and 2.70 mg of $FeCl_3 \cdot 6H_2O$ were respectively dissolved in 1 mL of deionized water to obtain a 10 mM stock solution, and 100 μL of the stock solution was diluted to 10 mL to obtain a 100 μM solution.

$Fe^{2+}/Fe^{3+}$ probe: 54.06 mg of phenanthroline was dissolved in 1 mL of DMSO to obtain a 300 μM stock solution, which can be used for detection without further dilution, 2.48 mg of the $Fe^{3+}$ probe was dissolved in 1 mL of DMSO to obtain a 10 mM stock solution, and 100 μL of the 10 mM stock solution was diluted to 100 μM in 10 mL of MeOH/$H_2O$ (v/v, 1:1).

$[Fe(phen)_3]^{2+}$ solution, 15 μL of a phenol stock solution was added to 15 mL of 100 μM $Fe^{2+}$ solution to obtain $[Fe(phen)_3]^{2+}$ complex.

Detection of $Fe^{2+}/Fe^{3+}$ with phen: the 100 μM of $Fe^{2+}/Fe^{2+}$ solution was further attenuated to 80, 60, 40, 20, 0 μM, 3 μL of a phenol stock solution was added to 3 mL of the above $Fe^{2+}/Fe^{3+}$ solution. Therefore, the final concentration of phenol was 300 μM and the concentration of Fe was hardly affected. UV-Vis absorption was detected at 510 nm.

Detection of $Fe^{2+}/Fe^{3+}$ with $Fe^{3+}$ probe. A 100 μM $Fe^{2+}/Fe^{3+}$ solution was further attenuated to 80, 60, 40, 20, 0 μM, 600 μl of $Fe^{2+}/Fe^{3+}$ solution and 2400 μL of $Fe^{3+}$ probe were mixed. Therefore, the final concentration of $Fe^{2+}/Fe^{3+}$ was 20, 16, 10, 8, 4, 0 μM, and the concentration of the $Fe^{3+}$ probe was 80 μM. The reaction system was incubated at 37° C. for 20 minutes, and detected at 450 nm with a UV-Vis spectrophotometer.

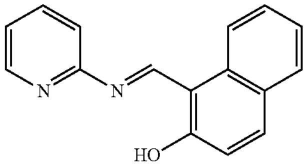

$Fe^{3+}$ probe 2.2 Detection of Copper Ions and Complexes $Cu^{2+}$ stock solution: 2.50 mg of $CuSO_4 \cdot 5H_2O$ was dissolved in 1 mL of deionized water to obtain a 10 mM stock solution.

$Cu^{2+}$ probe: 34.25 mg of sodium diethyldithiocarbamate was dissolved in 1 mL of DMSO to obtain a 200 mM stock solution.

Detection of $Cu^{2+}$ with sodium diethyldithiocarbamate: 100 μL of 10 mM $Cu^{2+}$ stock solution was diluted to 100 μM in 10 mL, and further attenuated to 80, 60, 40, 20, 0 μM, 3 μL of sodium diethyldithiocarbamate stock solution was added to 3 mL of the above $Cu^{2+}$ solution. Therefore, the final concentration of phen was 200 μM, and the concentration of $Cu^{2+}$ was hardly affected. UV-Vis absorption was detected at 450 nm.

2.3 Detection of nickel ions and complexes $Ni^{2+}$ stock solution: 2.38 mg of $NiCl_2 \cdot 6H_2O$ was dissolved in 1 mL of deionized water to obtain a 10 mM stock solution, and 100 μL of the 10 mM stock solution was diluted to 125 μM in 8 mL.

Dimethylglyoxime (DMG) solution: 89 mg of DMG was dissolved in 1.5 mL of 10 M NaOH (aq) to obtain a 0.51 M solution.

$K_2S_2O_8$ solution, 57 mg of $K_2S_2O_8$ was dissolved in 1.5 mL of deionized water to obtain a 0.14 mmol solution.

Detection of $Ni^2$+: 125 μM $Ni^{2+}$ solution was further attenuated to 100, 75, 50, 25, 0 μM, 50 μL of $K_2S_2O_8$ solution, 100 μL of 1M NaOH (aq), and 50 μL of DMG solution were sequentially added to 800 μL of $Ni^{2+}$ solution. Therefore, the final concentration of $Ni^{2+}$ was 100, 80, 60, 40, 20, 0 μM. The reaction system was incubated at 25° C. for 20 minutes, and detected at 530 nm with a UV-Vis spectrophotometer.

2.4 Detection of Ions/Complexes without Probes

A 10 mM stock solution of metal ions or complexes and corresponding compounds was prepared, and diluted to 100, 80, 60, 40, 20, 0 μM in sequence. Ions or complexes were detected by the following methods:

1. ICP-AES.

| Ions/complexes | Compounds |
|---|---|
| $Co^{2+}$ | $CoCl_2$ $6H_2O$ |
| $Pd^{2+}$ | $Pd(OAc)_2$ |
| $Ag^+$ | $Ag_2SO_4$ |

2. UV-Vis Spectral Detection:

| Ions/complexes | Compounds | Detection wavelength/nm |
|---|---|---|
| $Rh^{3+}$ | $RhCl_3{\bullet}3H_2O$ | 280 |
| $Ru^{3+}$ | $RuCl_3$ | 395 |
| $Fe(CN)_6^{3-}$ | $K_3Fe(CN)_6$ | 420 |
| $Co(NH_3)_6^{3+}$ | $Co(NH_3)_6Cl_3$ | 210 |
| $RuCl_6^{2-}$ | $K_2RuCl_6$ | 320 |
| $Ru(NH_3)_6^{3+}$ | $Ru(NH_3)_6Cl_3$ | 275 |
| $PdCl_4^{2-}$ | $K_2PdCl_4$ | 320 |
| $PtCl_6^{2-}$ | $K_2PtCl_6$ | 270 |
| $AuCl_4^-$ | $KAuCl_4$ | 250 |
| $IrCl_6^{2-}$ | $(NH_4)_2IrCl_6$ | 495 |

3. UPLC-MS

| Complexes | Compounds |
|---|---|
| Co(III) $VB_{12}$ | $VB_{12}$ |
| Pt(IV) | Pt(IV) complex 1 |

2.5 Detection of Ligand Release of Pt(IV) Complex 1 in Different Solutions

A 10 mM stock solution of Pt(IV) complex 1 was prepared, and diluted to 100 μM in $H_2O$. PBS, 5 mM Tyr, Trp, DMEM and CM (complete medium), FBS solution. After X-ray irradiation, 200 μL of ACN was added to each solution. The mixture was centrifuged, and the supernatant was then collected. The operation was repeated 2 more times, and the final concentration was ⅛ of the original concentration. Ligand release was detected by UPLC-MS and quantified by a standard curve of coumarin.

Figure 3:
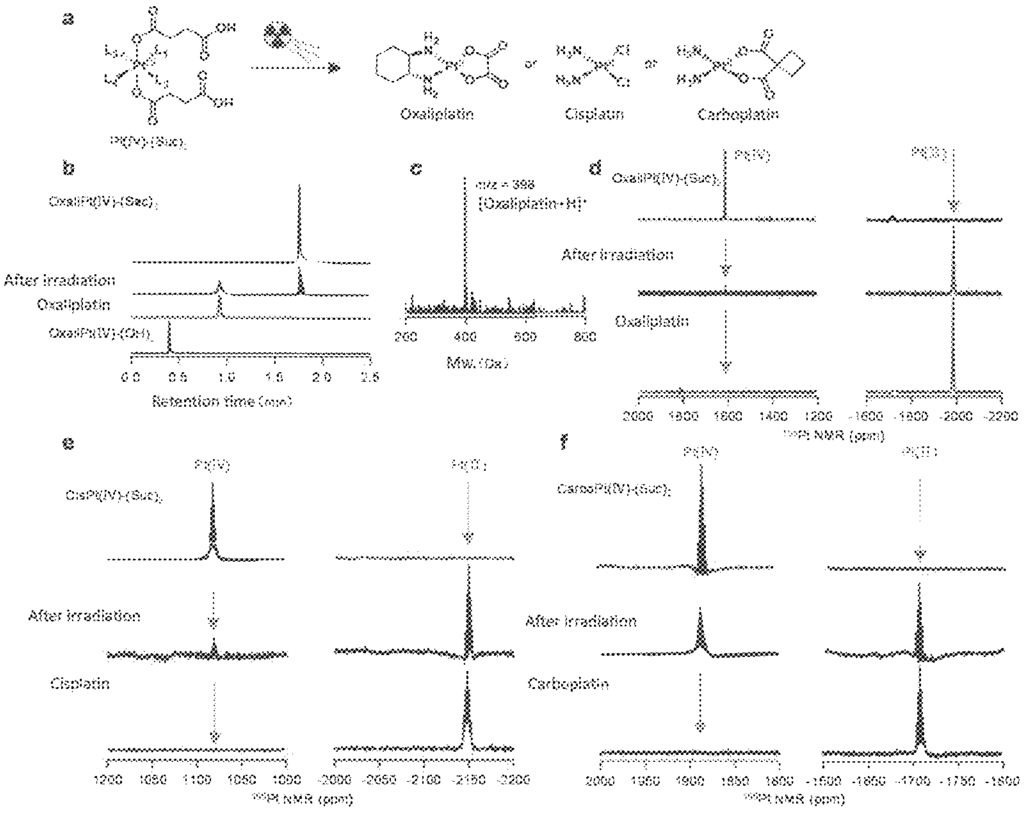
FIG. 3 depicts the broad-spectrum and high-efficiency release of FDA-approved Pt(II) drugs from Pt(IV) complexes driven by radiation.

2.6 Detection of the Release of the Corresponding Platinum Drug of Pt(IV)-$(Suc)_2$ $^{195}$Pt NMR was used for determination (FIG. 3, d e f)

Pt(IV)-$(Suc)_2$ was dissolved in 1 mL of deuterium water (80 mmol), and the mixture was adjusted to a pH of 7 with NaOH. After deoxygenation, the solution was exposed to 40 kGy γ-ray irradiation ($^{60}$Co source, 200 Gy/min, 200 min). After the reaction was completed, DMSO was added to redissolve the precipitate (for oxaliPt(IV)-$(Suc)_2$), or the clear solution after the reaction was directly used for $^{195}$Pt NMR determination (for cisPt(IV)$(Suc)_2$ and carboPt(IV)-$(Suc)_2$).

Determination of product by UPLC-MS (FIG. 3, b c)

OxaliPt(IV)-$(Suc)_2$ was dissolved in 1 mL of deionized water (1 mM), and the mixture was adjusted to a pH of 7 with $NaHCO_3$. After deoxygenation, the solution was exposed to 1 kGy γ-ray irradiation ($^{60}$Co source, 100 Gy/min, 10 min). The reaction crude product was analyzed by UPLC-MS, and the released product was determined to be Oxaliplatin by UPLC-MS.

2.7 Determination of Release Efficiency by UPLC-MS

Corresponding tetravalent platinum complexes (compounds 1-66) were dissolved in DMSO to obtain tetravalent platinum stock solutions (10 mM), and then diluted to 10 μM with pure water. After deoxygenation, the solution was subjected to 60 Gy X-ray irradiation (4 Gy/min, 15 min). The reaction crude product was analyzed by UPLC-MS, and the released product was determined to be the corresponding divalent platinum drug by UPLC-MS. The concentration of the divalent platinum drug was determined by the external standard curve of the platinum drug, and the release efficiency was calculated.

3. Biological Methods 3.1 Cell Culture

BGC823 cell line was acquired from the China National Cell Line Resource Infrastructure (Beijing. China). HCT116, Ls513, HT29, and LoVo were purchased from the American Type Culture Collection (ATCC). HCT116, Ls513, HT29 and BGC823 were grown in RPMI-1640 (Roswell Park Memorial Institute-1640) medium containing 10% FBS and 1% penicillin/streptomycin. LoVo cells were grown in Ham's F-12K (Roswell Park Memorial Institute-1640) medium containing 10% FBS and 1% penicillin/streptomycin. All cell cultures were cultivated at 37° C. and 5% $CO_2$.

3.2 Determination of Cell Viability

Cell viability was assessed with the CCK-8 test. Each test was repeated three times.

In order to detect the cytotoxicity of oxaliPt(IV)-$(OAc)_2$, HCT116, Ls513, LoVo, HT29 and BGC823 were inoculated in 200 μL of RPMI-1640 or F-12K medium containing 10% FBS and 1% penicillin/streptomycin at a concentration of $5{\times}10^4$/mL on a 96-well plate. The plate was incubated in a 5% $CO_2$ incubator at 37° C. for 24 hours. Cells were then incubated with 10 μM oxaliPt(IV)-$(OAc)_2$ under hypoxia for 24 hours. Cells were then irradiated with 8 Gy X-rays and incubated for an additional 3 days. After the incubation was completed, blank medium containing CCK-8 with a final concentration of 0.5 mg/mL was added to the cells. The 96-well plate was further incubated at 37° C., 5% $CO_2$ for 2 hours, and the absorbance was measured at 450 nm. The absorbance of the treated cells was compared to that of the control group, where the survival rate of the untreated control group was set as 100%.

3.3 Tumor Model

All animal tests were performed in accordance with guidelines approved by the Peking University Ethics Committee.

6-week-old female Nu/Nu mice were ordered from the Vital River Laboratory (Beijing, China) and grown under specific pathogen-free, adequate water and food conditions. 100 μL of PBS containing $2{\times}10^6$ HCT116 cells was injected subcutaneously into the right shoulder of mice to construct a tumor xenograft model. Tumor volume was equal to ½ length*width$^2$.

Figure 5:
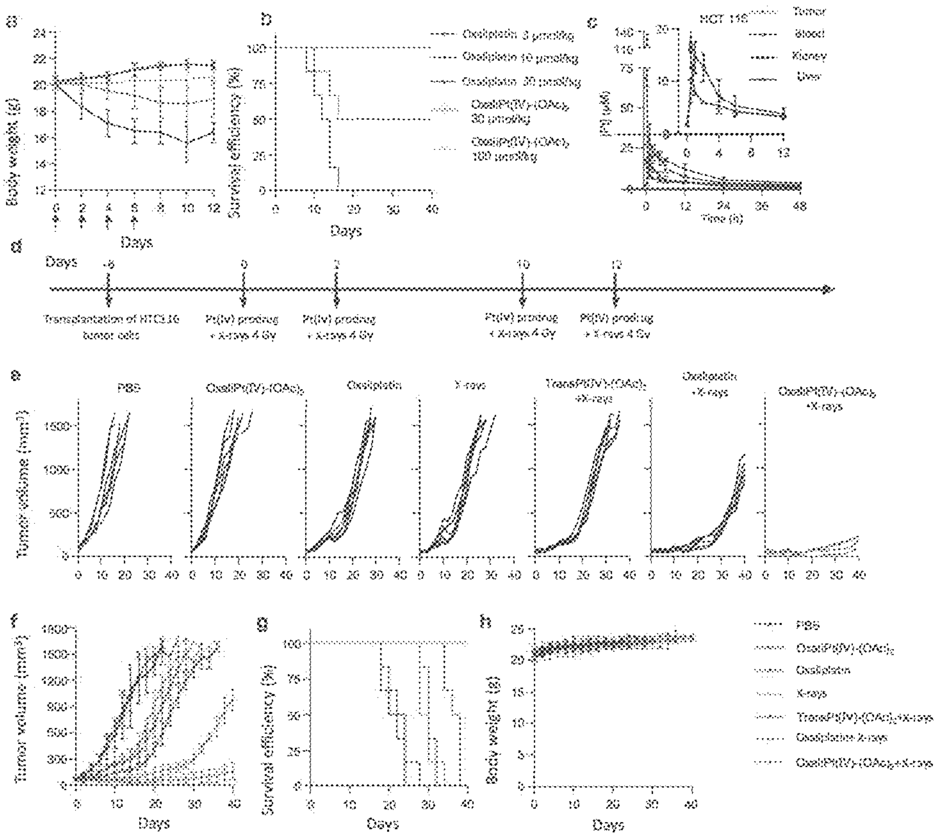
FIG. 5 depicts that the radiotherapy-driven reduction of an oxaliPt(IV)-$(OAc)_2$ prodrug releases Oxaliplatin for the chemotherapy of an Oxaliplatin-sensitive cell line HCT116 tumor to achieve combined radiotherapy and chemotherapy.

Treatment was initiated when the tumor volume reached 50 $mm^3$ (about 6 days), and the treatment schedule was shown in FIG. 5. According to the pharmacokinetics of oxaliPt(IV)-$(OAc)_2$, 1 hour after the injection of the prodrug, the mice received radiotherapy, that is, the tumor area was irradiated with 4 Gy of X-rays. The body weight and tumor size of mice were recorded every third day. When the tumor size of the mice exceeded 1500 $mm^3$, the mice were euthanized according to the guidance of the ethics committee. Recording was continued until day 40 after the mice were started to be treated.

Influence of Radiotherapy Dose on Metal Reduction Efficiency 10-500 kGy of radiation is typically used in industry to treat wastewater for the precipitation of toxic heavy metal ions in polluted water. Therefore, this study first tried to irradiate $FeCl_3$ (100 μM, aq) solution with 10-60 Gy (clinical radiotherapy dose) of X-rays (FIG. 1*a*). 1,10-Phenanthroline is a classic probe for detecting $Fe^{3+}/Fe^{2+}$ redox reaction, wherein the aqueous solution of $Fe(phen)^{33}$ is colorless, while the aqueous solution of $Fe(phen)_3^{2+}$ is orange-red. When 1,10-phenanthroline (30 mM, DMSO) was added to the $FeCl_3$ solution immediately after irradiation (the final concentration of 1,10-phenanthroline was 300 μM), the solution immediately turned orange-red (FIG. 1*b*), showing that $Fe^{2+}$ was generated. As determined by the standard curve of $Fe(phen)_3^{2+}$, the yield of $Fe^{2+}$ had a linear relationship with the absorbed dose of radiation (FIG. 1*c*). In addition, quantitative detection of $Fe^{3+}$ revealed that the consumption of $Fe^{3+}$ was almost equal to the generation of $Fe^{2+}$ (FIG. 1*c*). Therefore, $Fe^{2+}$ was the main product of the radiation reduction of $Fe^{3+}$.

Hydrated electrons are one of the strongest reducing agents in water (standard electrode potential, −2.77 V) and also one of the main products of water radiolysis (~280 nM/Gy). We hypothesize that the radiation-driven metal reduction is mediated by $e_{aq}^-$ produced by water radiolysis. As evidenced by the results that $Fe^{3+}$ was irradiated in 10 mM methanol, tert-butanol and sodium formate solutions to produce $Fe^{2+}$, a reducing environment (quencher for $^-OH$) was favorable for this reaction to occur. However, $NaNO_3$ and saturated oxygen solution, i.e., known $e_{aq}^-$ quenchers, greatly reduced the amount of $Fe^2$ released (FIG. 1*d*). The $e_q$-mediated reduction should be generally applicable to most transition metals. Therefore, a series of representative metal ions (100 μM, aq) were tested under the same conditions (X-rays at 60 Gy), and the reduction yield was determined by the absorbance of the corresponding complex or other methods. As shown in FIG. 1*e*, radiation-driven reduction reactions were feasible in most cases. The yield of irradiated metal reduction was as high as 240 nM/Gy, which was close to the theoretical yield of $e_{aq}^-$.

FIG. 1 illustrates the broad-spectrum nature of radiation reduction of metal ions. 1,10-phenanthroline (phen) was used to detect $Fe^{3+}/Fe^{2+}$ redox reaction. After the $Fe^{3+}$ solution was irradiated by X-rays (0~60 Gy), phen was added immediately to quantitatively form an orange-red complex with Fe(II) ($\lambda_{max}$=510 nm), which proved the radiation-driven reduction of $Fe^{3+}$ (100 μM, aq) to $Fe^{2+}$. Schematic (FIG. 1*a*) and photograph (FIG. 1*b*) showed titration staining for radiation-driven reduction. FIG. 1*c*, the disappearance of $Fe^{3+}$ was almost equal to the generation of $[Fe(phen)_3]^{2+}$, which had a linear relationship with the absorbed radiation dose. The G value was 200 nM/Gy, which was close to the theoretical G value (280 nM/Gy) of $e_{aq}^-$. FIG. 1*d*, The radiation-driven reduction yield of $Fe^{3+}/Fe^{2+}$ increased when treated with a hydroxyl radical quencher and decreased when treated with an $e_{aq}^-$ quencher. FIG. 1*e*, Radiation-driven reduction of metal ions was generally applicable to transition metals.

Subsequently, this study further explored the feasibility of radiation reduction of metal complexes. The reduction potential of the metal complex may be altered, leading to a reduction in the reactivity of the radiation reduction. Therefore, 100 μM metal complexes were prepared and irradiated with 0-60 Gy of X-rays after deoxidation. It was gratifying that the metal complexes had also achieved good results. According to the standard curves of the individual metal complex, the yields of the radiation-driven metal reduction exceeded 200 nM/Gy and can be as high as 350 nM/Gy for some metals (FIG. 2*a*), exceeding the theoretical yield of $e_{aq}^-$. This is because metal atoms with high atomic numbers can deposit more X-ray energy, thus amplifying the ionizing radiation dose. Therefore, the radiation reduction reaction of metals has broad-spectrum, highly efficient, and highly selective nature, promising to be developed as a tool for cleavage chemistry in vivo.

In addition, UPLC-MS analysis after radiation reduction of Pt(IV) complex 1 detected the release of axial ligands. Due to the high clinical application potential of Pt(IV) derivatives, the next step is to test the role of radiation reduction in a biological environment, that is, to achieve radiotherapy-driven activation of Pt(IV) original drug in tumors. To test biocompatibility, the Pt(IV) complex was dissolved in PBS, 5 mM Tyr, 5 mM Trp, Dulbecco's Modified Eagle Medium (DMEM) and Complete Medium (CM), irradiated, and then analyzed by UPLC-MS. As shown in FIG. 2*b*, the release of axial ligands by Pt(IV) complex 1 was achieved in all of the above solutions. Even in complete fetal bovine serum (FBS), the reaction yield was not much different from that in water Therefore, the strategy of radiation reduction of Pt(IV) complex 1 to release axial ligands was also highly feasible under complex conditions in vivo.

Figure 2:
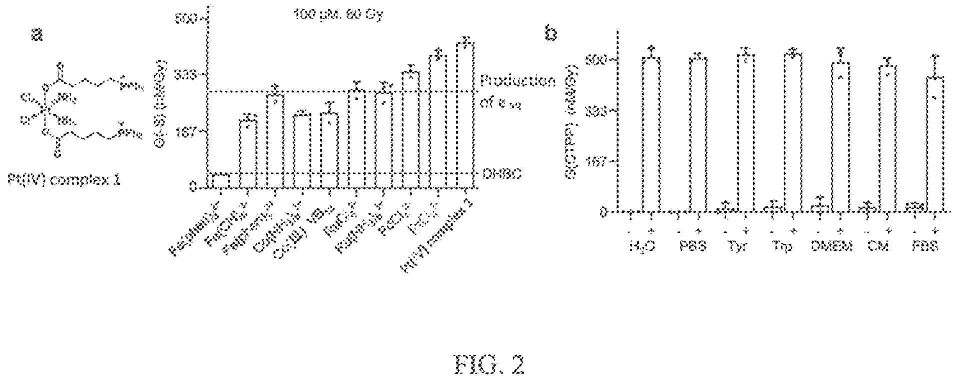
FIG. 2 depicts the broad-spectrum of radiation reduction of metal complexes.

FIG. 2 illustrates the broad-spectrum of reduction of metal complexes by radiation. FIG. 2*a*, transition metal complexes could also be reduced by medical doses of radiation, and the reduction yield was higher than the theoretical yield of $e_{aq}^-$. At the same time, the axial ligands could be released after the Pt(IV) complex (left panel, 100 μM, 1% DMSO in water) was reduced by radiation. FIG. 2*b*, under various biological conditions (Tyr was tyrosine, Trp was tryptophan, 5 mM; DMEM, culture medium, CM, complete medium; FBS, fetal bovine serum), the Pt(IV) complex (100 μM) was reduced by radiation, and the corresponding ligand release was detected by UPLC.

There are two possibilities for this radiation-driven release mechanism. The axial ligand release of the Pt(IV) complex can be achieved by hydrolysis or reduction: hydrolysis breaks the ester bond to obtain $Pt(IV)-(OH)_2$ and the axial ligands; while the reduction changes the valence state of the platinum element to generate the corresponding divalent platinum drug. According to the ligand field theory, the most common coordination number of Pt(IV) having $5d^6$ valence electron configuration is 6, while Pt(II) having $5d^8$ valence electron configuration tends to form tetragonal complexes. Existing studies on Pt(IV) prodrugs have shown that the reduction of Pt(IV) to Pt(II) will lead to decrease in the coordination number and the release of a ligand.

In order to explore the reaction process, the solution of $oxaliPt(IV)-(Suc)_2$ (80 mM, $D_2O$) was deoxygenated and then subjected to irradiation with 40 kGy of γ-rays ($^{60}Co$ source, 200 Gy/min, 200 min, FIG. 3*a*). The irradiated solution was detected by UPLC-MS, and only one new peak was observed, wherein the retention time (FIG. 3*b*) and mass spectrometry signal (FIG. 3*c*) were both consistent with those of the oxaliplatin standard sample. The product was analyzed by nuclear magnetic resonance (NMR). $^{195}Pt$-NMR showed that the peak of the Pt(IV) complex at 1615 ppm almost disappeared after irradiation (FIG. 3*d* top), and a new singlet peak appeared at −1988 ppm (FIG. 3*d* middle), which was within the chemical shift range of the Pt(II) complex and coincided with that of oxaliplatin (FIG. 3*d* bottom). The above tests all proved that the release of axial ligands was caused by radiation reduction of Pt(IV) rather than hydrolysis.

To explore the generalizability of this strategy, we further conducted the same study on two other platinum-based drugs commonly used globally, carboplatin and cisplatin. NMR characterization revealed that $cisPt(IV)-(Suc)_2$ and $carboPt(IV)-(Suc)_2$ would release the corresponding Pt(II) drugs after γ-ray irradiation in $D_2O$ (FIG. 3*e, f*). In view of the wide application of platinum-based drugs in chemotherapy, the strategy proposed in this work to control the release of Pt(II) by radiation-driven reduction of Pt(IV) prodrugs is very promising in realizing precision chemotherapy driven by radiotherapy.

FIG. 3 exemplifies the broad-spectrum and high-efficiency release of FDA-approved Pt(II) drugs from Pt(IV) complexes driven by radiation. a. Schematic illustration of release of Pt(II) drugs from Pt(IV) complexes driven by radiation. b. UPLC chromatograms of oxaliPt(IV)-$(Suc)_2$, oxaliPt(IV)-$(Suc)_2$+ radiation, oxaliplatin and oxaliPt(IV)-$(OH)_2$, where oxaliplatin and oxaliPt(IV)-$(OH)_2$ were used as references. The main released product of oxaliPt(IV)-$(Suc)_2$ driven by radiation had the same retention time as that of oxaliplatin. The detector wavelength was set at 254 nm. c, MS of the product released from oxaliPt(IV)-$(Suc)_2$ driven by radiation showed that the released product was oxaliplatin. d-f, Study of Pt(II) drugs released from Pt(IV) complexes by nuclear magnetic resonance (NMR). d, $^{195}$Pt-NMR spectra of oxaliPt(IV)-$(Suc)_2$ (1615 ppm, top), radiation product (−1988 ppm, middle) and external standard (bottom). e, $^{195}$Pt-NMR spectra of cisPt(IV)-$(Suc)_2$ (1082 ppm, top), radiation product (−2150 ppm, middle) and external standard (bottom). f, $^{195}$Pt-NMR spectra of carboPt (IV)-$(Suc)_2$ (1883 ppm, top), irradiation product (1707 ppm, middle) and external standard (bottom). $^{195}$Pt-NMR spectrum showed that the release of FDA-approved Pt(II) drugs driven by radiation is effective and generally applicable to Pt(IV) complexes.

The key to developing a successful prodrug is to balance the requirements for stability and reactivity under physiological conditions. The fatal disadvantage of metal complexes in chemotherapy drugs is their limited biological stability. In fact, for most of the Pt(IV) prodrugs reported so far, active Pt(II) anticancer drugs can be released just under intracellular bioreductive conditions. Therefore, the biological stability of Pt(IV) prodrugs is an important prerequisite for the realization of this strategy. Based on the existing research, tetracarboxy Pt(IV) has significant stability advantages. Therefore, we further designed oxaliPt(IV)-$(OAc)_2$ (FIG. 4*a*), because oxaliPt(IV)-$(Suc)_2$ cannot be effectively enriched in tumors because it has two carboxyl groups as axial ligands and has two negative charges in the physiological environment in vivo. However, the corresponding oxaliPt(IV)-$(OAc)_2$ has good stability and reactivity. After co-incubation with 20 equivalents of Vc for 24 hours, more than 95% of oxaliPt(IV)-$(OAc)_2$ was still very stable. (FIG. 4*b*). After OxaliPt(IV)-$(OAc)_2$ (10 μM PBS solution, deoxygenated) was irradiated with 0-60 Gy X-rays, it was found that the released Oxaliplatin was positively correlated with the given radiation dose (FIG. 4*c*). Compared with Oxaliplatin, OxaliPt(IV)-$(OAc)_2$ is 2 to 3 orders of magnitude less toxic to Oxaliplatin-sensitive cell lines, such as HCT116, HT29, LoVo and Ls513 (human colorectal cancer cell lines), with an $IC_{50}$ of about submicromolar level.

In order to examine whether Oxaliplatin is released in the cellular environment as driven by radiation and exerts its anticancer function, we performed cell viability test of oxaliPt(IV)-$(OAc)_2$+X-rays on several cell lines. In this test, the complete medium was used as a control, and cells were treated with 8 Gy X-rays, 10 μM oxaliPt(IV)-$(OAc)_2$, and 10 μM oxaliPt(IV)-$(OAc)_2$+8 Gy X-rays, respectively. After culturing for 96 hours, CCK-8 detection showed that the cell viability of the group treated with 10 μM oxaliPt(IV)-(OAc) $_{2+8}$ Gy X-rays was significantly lower than that of the group treated with only 10 μM oxaliPt(IV)-$(OAc)_2$ or 8 Gy X-rays (FIG. 4*d*), indicating the feasibility of the strategy of releasing Oxaliplatin from oxaliPt(IV)-$(OAc)_2$ in cells.

Figure 4:
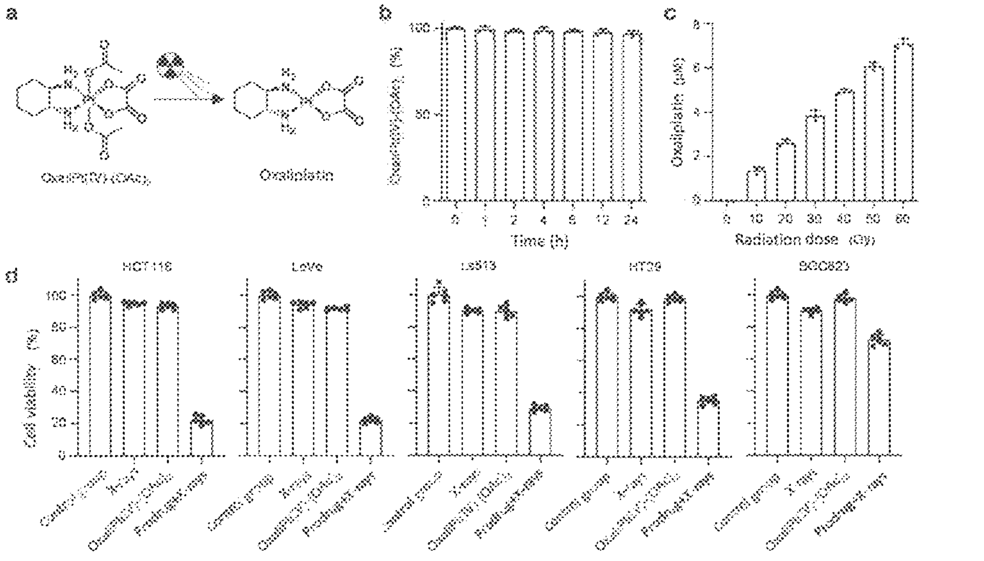
FIG. 4 depicts radiation-induced effective controlled release of Oxaliplatin in living cells.

FIG. 4 illustrates that radiation-induced controlled release of Oxaliplatin is effective in living cells. FIG. 4*a*, Schematic illustration of radiotherapy-driven release of Oxaliplatin, a widely used chemotherapeutic drug, from the prodrug oxaliPt(IV)-$(OAc)_2$. FIG. 4*b*, Stability of the prodrug OxaliPt (IV)-$(OAc)_2$. When 10 μM oxaliPt(IV)-$(OAc)_2$ was incubated with 20 equivalents of Vc (200 μM), more than 95% of oxaliPt(IV)-$(OAc)_2$ remained stable after 24 hours. FIG. 4*c*, Oxaliplatin released from 10 μM oxaliPt(IV)-(OAc) at clinically relevant doses (0-60 Gy. X-rays), with efficiencies as high as 70%. FIG. 4*d*, Cell viability test of in vitro controlled release of Oxaliplatin (prodrug: [oxaliPt(IV)-$(OAc)_2$]=10 μM (h); X-ray, 8 Gy; n=6). HCT116, LoVo, Ls513, and HT69 are human colorectal cancer cells that are sensitive to Oxaliplatin.

In order to find the optimal dosage, we evaluated the effect of different doses of Oxaliplatin and prodrug on the health of healthy mice. In the same dosing way as in the treatment, the mice were dosed every third day, and then the body weight curve was recorded. It can be seen that the injection of 3 μmol/kg Oxaliplatin or 30 μmol/kg oxaliPt (IV)-$(OAc)_2$ did not reduce the body weight of mice, but more than 10 μmol/kg Oxaliplatin and 100 μmol/kg of oxaliPt(IV)-$(OAc)_2$ exhibited significant side effects, leading to weightlessness in mice (FIG. 5*a*). When the dose of Oxaliplatin reached 30 μmol/kg, the mice lost severe weight and started to die on the 8th day, and all died on the 16th day (FIG. 5*b*). From the long-term survival curve and body weight curve of mice, it can be concluded that 3 μmol/kg Oxaliplatin and 30 μmol/kg oxaliPt(IV)-$(OAc)_2$ have no apparent side effects and can be used as appropriate dosages. In order to achieve the best effect of radiotherapy and chemotherapy, we used ICP-MS to study the pharmacokinetics of oxaliPt(IV)-$(OAc)_2$ in HCT116 tumor-bearing mice to explore the optimal radiotherapy time. After injecting 30 μmol/kg of oxaliPt(IV)-$(OAc)_2$ into HCT116 tumor-bearing mice via tail vein injection, the mice were sacrificed at the selected time. Then ICP-MS was used to detect the concentration of the platinum drug in blood, tumor, liver and kidney respectively. ICP-MS data at multiple time points showed that the prodrug was mainly metabolized by the liver and kidney, and the tumor uptake peaked at 1 hour after administration (about 15 μM), then gradually decreased, and was completely cleared 48 hours after injection (FIG. 5*c*). One hour after administration, the mice had lower concentrations of the prodrug in muscle and brain, suggesting that the drug did not cause side effects in these organs.

The radiation-mediated release of Oxaliplatin in mice and the corresponding efficacy were then further evaluated. HCT116 cells were implanted into the right flank of Nu/Nu mice until the average tumor volume reached about 50 mm$^{r}$ Mice were randomly divided into 7 groups, including control group (PBS only), and groups treated with 3 μmol/kg Oxaliplatin, 30 μmol/kg oxaliPt(IV)-$(OAc)_2$, X-ray, 3 μmol/kg Oxaliplatin+X-ray, 30 μmol/kg oxaliPt(IV)-$(OAc)_2$+X-ray, and 3 μmol/kg transPt(IV)-$(OAc)_2$+X-ray. Mice were injected with the drug on day 0 (FIG. 5*d*). For the treatment group, 4 Gy of X-rays were given 1 hour after the injection, and the treatment cycle was repeated on days 10-12. By 18 days after the start of treatment, the tumor size of the control group reached 1500 mm, while a single injection of 30 μmol/kg oxaliPt(IV)-$(OAc)_2$ had no significant effect on tumor growth, and tumors in the 30 μmol/kg oxaliPt(IV)-$(OAc)_2$+X-ray group were significantly inhibited (FIG. 5*e, f*) and the survival time of mice was increased (FIG. 5*g*), which indicated that the therapeutic effect was caused by radiation-mediated release of Oxaliplatin. At the same time, mice in the oxaliPt(IV)-$(OAc)_2$+X-ray treatment group did not lose body weight (FIG. 5*h*), indicating that our strategy has good biological safety. Therefore, the treatment results on HCT116 tumor-bearing mice indicated that the present radiation-driven release of Pt(II) drugs is highly feasible in vivo.

FIG. 5 illustrates that radiotherapy-driven reduction of the oxaliPt(IV)-$(OAc)_2$ prodrug releases Oxaliplatin for chemotherapy of Oxaliplatin-sensitive cell line HCT116 tumor to achieve combined radiotherapy and chemotherapy. Body weight change curve (FIG. 5*a*) and survival curve (FIG. 5*b*) of mice after intravenous injection of different doses of oxaliPt(IV)-$(OAc)_2$ and Oxaliplatin were shown. Drug adaptation studies on nude mice showed that the maximum tolerated doses of Oxaliplatin and oxaliPt(IV)-$(OAc)_2$ were about 3 μmol/kg and 30 μmol/kg, respectively. FIG. 5*c* shows pharmacokinetics of the prodrug oxaliPt(IV)-$(OAc)_2$ to determine the optimal timing of radiotherapy. Tumor uptake of the prodrug OxaliPt(IV)-$(OAc)_2$ peaked at 1-2 hours after injection and then gradually declined. The remainder of the prodrug was rapidly cleared from the blood and excreted through the renal and hepatobiliary systems. FIG. 5*d* shows treatment regimen. FIGS. 5 *e-h* show radiotherapy-driven release of Oxaliplatin for tumor treatment (n=6 mice per group). *e*, Tumor volume in individual mouse. *f*, Mean volume of tumors. The prodrug was injected intravenously for a total of 4 injections at a dose of 30 μmol/kg. One hour after intravenous injection, the tumor site in the irradiation group was irradiated with 4 Gy X-rays. Tumor volume in each group was measured every two days for 40 days. *g*, Survival curves of mice. According to the guidelines of Peking University Animal Ethics Committee, mice were sacrificed when the tumor volume reached 1500 $mm^3$. *h*, Body weight curves of mice. No significant side effects were observed, highlighting the biological safety of this novel therapeutic strategy.

In this study, radiation-induced metal reduction in vivo was achieved, thereby constructing a new in vivo cleavage chemistry. By applying this strategy to the activation of Pt(IV) prodrugs, radiotherapy becomes an exogenous stimulus that triggers drug release, thereby completing the release of chemotherapeutic drugs at the tumor site under the guidance of precise radiotherapy. In addition, this strategy is also helpful to solve the problem of radiotherapy resistance in hypoxic tumors, and instead can improve the drug release efficiency under hypoxic conditions. The direct metal reduction of $e_{aq}^-$ induced by radiation can also be extended to other metals or biological complexes (such as metalloproteins), providing an efficient tool for the mechanistic dissection of complex biological processes.

From the above description, one skilled in the art can easily ascertain the essential characteristics of the present disclosure, and without departing from the spirit and scope of the present disclosure, they can make various changes and modifications to the present disclosure to adapt it to various usages and conditions. Accordingly, other examples are also within the scope of the attached claims.

This application claims the priority of the Chinese patent application No. 202011337782.X filed on Nov. 25, 2020, and the content disclosed in the above Chinese patent application is incorporated in its entirety as a part of this application.

What is claimed is:

1. A Pt(IV) complex of formula (I), which is used as a prodrug activated by radiation for the treatment of a tumor,

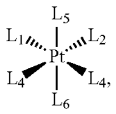

(I)

wherein $L_1$ to $L_6$ are ligands of platinum; the complex can release $L_5$ and $L_6$ to obtain a Pt(II) complex of formula (II) after irradiation,

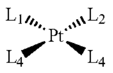

(II)

wherein the Pt(II) complex of formula (II) is Cisplatin, Carboplatin, Nedaplatin, Oxaliplatin, Lobaplatin, or Heptaplatin, wherein, (i)

$L_5$ is $^-$O—C(O)—R, wherein R is each independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, eicosyl;

$L_6$ is $^-$O—C(O)—R, wherein R is each independently selected from (dimethylamino) methylene, 2-(dimethylamino) ethylene, 3-(dimethylamino) propylene, 4-(dimethylamino) butylene, 5-(dimethylamino) pentylene, 6-(dimethylamino) hexylene, 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene, methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino;

or (ii)

$L_5$ is $^-$O—C(O)—R, wherein R is each independently selected from carboxymethylene, 2-carboxyethylene, 3-carboxypropylene, 4-carboxybutylene, 5-carboxypentylene, 6-carboxyhexylene;

$L_6$ is $^-$O—C(O)—R, wherein R is each independently selected from (dimethylamino) methylene, 2-(dimethylamino) ethylene, 3-(dimethylamino) propylene, 4-(dimethylamino) butylene, 5-(dimethylamino) pentylene, 6-(dimethylamino) hexylene, 5-maleimidopentylene, 6-maleimidohexylene, 7-maleimidoheptylene, 8-maleimidooctylene, 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene;

or (iii)

$L_5$ is $^-$O—C(O)—R, wherein R is each independently selected from (dimethylamino) methylene, 2-(dimethylamino) ethylene, 3-(dimethylamino) propylene, 4-(dimethylamino) butylene, 5-(dimethylamino) pentylene, 6-(dimethylamino) hexylene;

$L_6$ is $^-$O—C(O)—R, wherein R is each independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, eicosyl, carboxymethylene, 2-carboxyethylene, 3-carboxypropylene, 4-carboxybutylene, 5-carboxypentylene, 6-carboxyhexylene, (dimethylamino) methylene, 2-(dimethylamino) ethylene, 3-(dimethylamino) propylene, 4-(dimethylamino) butylene, 5-(dimethylamino) pentylene, 6-(dimethylamino) hexylene, 5-maleimidopentylene, 6-maleimidohexylene, 7-maleimidoheptylene, 8-maleimidooctylene, 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene, methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino;

or (iv)

$L_5$ is $^-$O—C(O)—R, wherein R is each independently selected from 5-maleimidopentylene, 6-maleimidohexylene, 7-maleimidoheptylene, 8-maleimidooctylene;

$L_6$ is $^-$O—C(O)—R, wherein R is each independently selected from carboxymethylene, 2-carboxyethylene, 3-carboxypropylene, 4-carboxybutylene, 5-carboxypentylene, 6-carboxyhexylene, (dimethylamino) methylene, 2-(dimethylamino) ethylene, 3-(dimethylamino) propylene, 4-(dimethylamino) butylene, 5-(dimethylamino) pentylene, 6-(dimethylamino) hexylene, 5-maleimidopentylene, 6-maleimidohexylene, 7-maleimidoheptylene, 8-maleimidooctylene, 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene, methylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino;

or (v)

$L_5$ is $^-$O—C(O)—R, wherein R is each independently selected from 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene;

$L_6$ is $^-$O—C(O)—R, wherein R is each independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, eicosyl, carboxymethylene, 2-carboxyethylene, 3-carboxypropylene, 4-carboxybutylene, 5-carboxypentylene, 6-carboxyhexylene, (dimethylamino) methylene, 2-(dimethylamino) ethylene, 3-(dimethylamino) propylene, 4-(dimethylamino) butylene, 5-(dimethylamino) pentylene, 6-(dimethylamino) hexylene, 5-maleimidopentylene, 6-maleimidohexylene, 7-maleimidoheptylene, 8-maleimidooctylene, 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene, methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino;

or (vi)

$L_5$ is-O—C(O)—R, wherein R is each independently selected from methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino;

$L_6$ is $^-$O—C(O)—R, wherein R is each independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecanyl, octadecyl, nonadecanyl, eicosyl, (dimethylamino) methylene, 2-(dimethylamino) ethylene, 3-(dimethylamino) propylene, 4-(dimethylamino) butylene, 5-(dimethylamino) pentylene, 6-(dimethylamino) hexylene, 3-(4-iodophenyl) propylene, 3-(3-iodophenyl) propylene, 3-(3,5-diiodophenyl) propylene, 3-(4-bromophenyl) propylene, 3-(3-bromophenyl) propylene, 3-(3,5-dibromophenyl) propylene, methylamino, ethylamino, propylamino, butylamino, amylamino, hexylamino, heptylamino, octylamino, nonylamino, decylamino, undecylamino, dodecylamino, tridecylamino, tetradecylamino, pentadecylamino, hexadecylamino, heptadecanylamino, and octadecylamino.

2. The Pt(IV) complex of claim 1, wherein the tumor is leukemia, lung cancer, malignant lymphoma, breast cancer, ovarian cancer, soft tissue sarcoma, osteosarcoma, rhabdomyosarcoma, Ewing sarcoma, blastoma, neuroblastoma, bladder cancer, thyroid cancer, prostate cancer, head and neck cancer, nasopharyngeal carcinoma, esophageal cancer, testicular cancer, stomach cancer, liver cancer, pancreatic cancer, cervical cancer, endometrial cancer, melanoma, or colorectal cancer.

3. A pharmaceutical composition comprising the Pt(IV) complex of claim 1.

4. A method for treating a tumor, comprising:

administering to a subject the Pt(IV) complex of claim 1, and irradiating the subject.

5. The method of claim 4, wherein the irradiation is from radiotherapy.

6. The method of claim 5, wherein the radiotherapy is performed 0.5-3 h after administration.

7. The method of claim 5, wherein the radiation dose is less than 60 Gy.

8. The method of claim 4, wherein the tumor is leukemia, lung cancer, malignant lymphoma, breast cancer, ovarian cancer, soft tissue sarcoma, osteosarcoma, rhabdomyosarcoma, Ewing sarcoma, blastoma, neuroblastoma, bladder cancer, thyroid cancer, prostate cancer, head and neck cancer, nasopharyngeal carcinoma, esophageal cancer, testicular cancer, stomach cancer, liver cancer, pancreatic cancer, cervical cancer, endometrial cancer, melanoma, or colorectal cancer.

9. A kit comprising:

the Pt(IV) complex of claim 1, and description, indicating that the administration is followed by radiation therapy to treat a tumor.

10. A kit comprising:

the pharmaceutical composition of claim 3, and description, indicating that the administration is followed by radiation therapy to treat a tumor.

11. The pt(IV) complex of claim 1, having the structure of
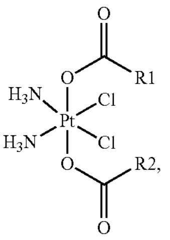
wherein:
| | |
|---|---|
| $R_1$ = 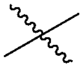 | $R_2$ = 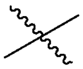 |
| $R_1$ = 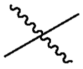 | $R_2$ = 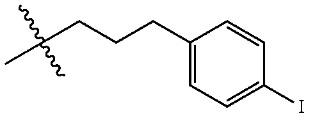 |
| $R_1$ = 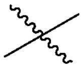 | $R_2$ = 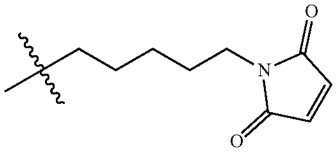 |
| $R_1$ = 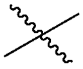 | $R_2$ = 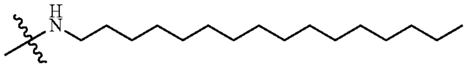 |
| $R_1$ = 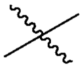 | $R_2$ = 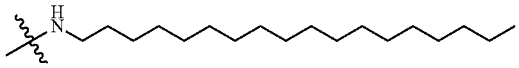 |
| $R_1$ = 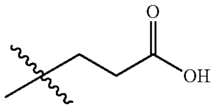 | $R_2$ = 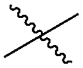 |
| $R_1$ = 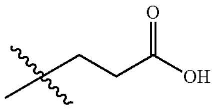 | $R_2$ = 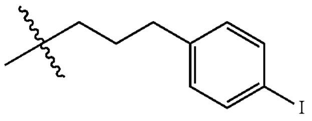 |
| $R_1$ = 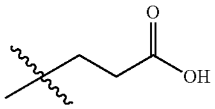 | $R_2$ = 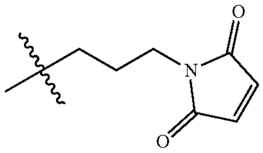 |
| $R_1$ = 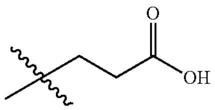 | $R_2$ = 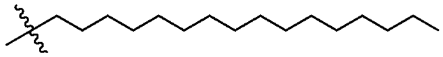 |
| $R_1$ = 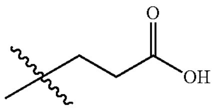 | $R_2$ = 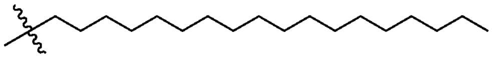 [SMILES: *CCCCCCCCCCCCCCCCCC] |

-continued
| | |
|---|---|
| $R_1$ = 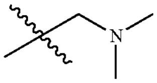 | $R_2$ = 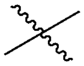 |
| $R_1$ = 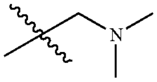 | $R_2$ = 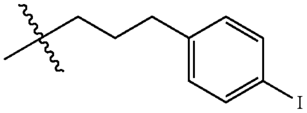 [SMILES: *CCCc1ccc(I)cc1] |
| $R_1$ = 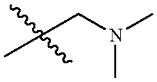 | $R_2$ = 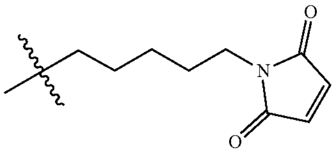 |
| $R_1$ = 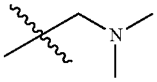 | $R_2$ = 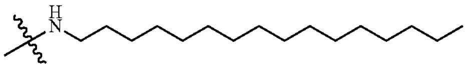 |
| $R_1$ = 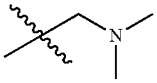 | $R_2$ = 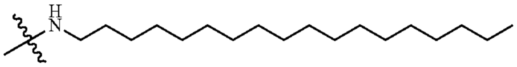 |
| $R_1$ = 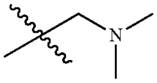 | $R_2$ = 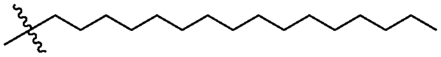 |
| $R_1$ = 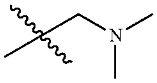 | $R_2$ = 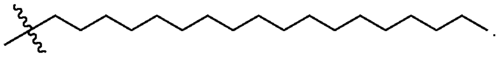. |
12. The pt(IV) complex of claim 1, having the structure of
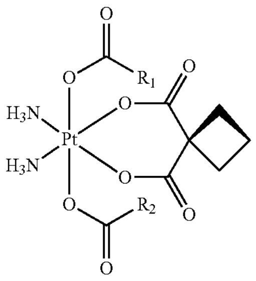
wherein:
| | |
|---|---|
| $R_1$ = 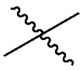 | $R_2$ = 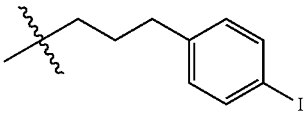 [SMILES: *CCCc1ccc(I)cc1] |
| $R_1$ = 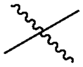 | $R_2$ = 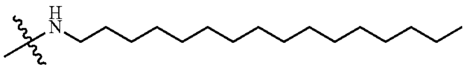 |
| $R_1$ = 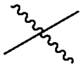 | $R_2$ = 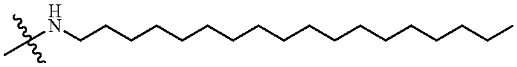 |

-continued
$R_1$ = 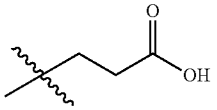 $R_2$ = 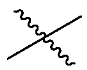
$R_1$ = 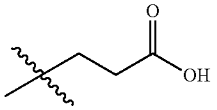 $R_2$ = 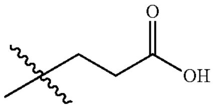
$R_1$ = 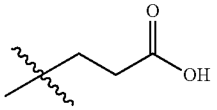 $R_2$ = 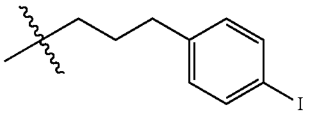
$R_1$ = 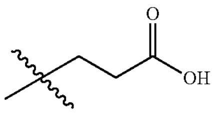 $R_2$ = 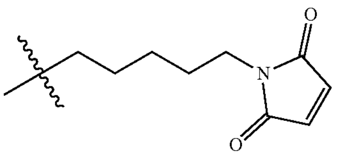 [SMILES: *CCCCCN1C(=O)C=CC1=O]
$R_1$ = 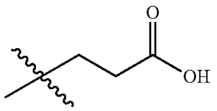 $R_2$ = 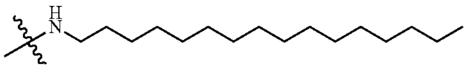
$R_1$ = 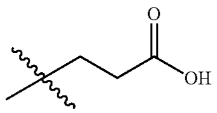 $R_2$ = 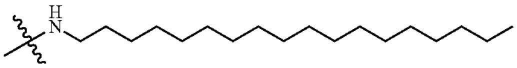
$R_1$ = 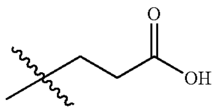 $R_2$ = 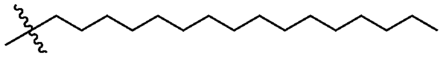
$R_1$ = 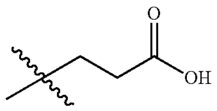 [SMILES: *CCC(=O)O] $R_2$ = 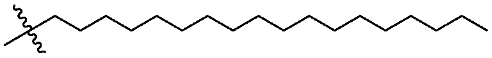
$R_1$ = 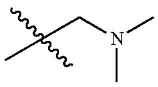 [SMILES: *CN(C)C] $R_2$ = 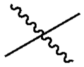
$R_1$ = 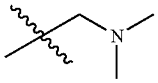 $R_2$ = 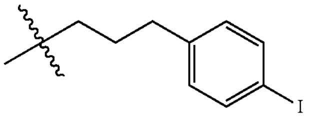
$R_1$ = 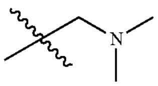 [SMILES: *CN(C)C] $R_2$ = 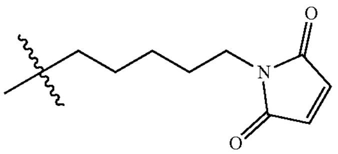
$R_1$ = 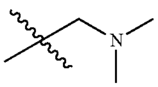 [SMILES: *CN(C)C] $R_2$ = 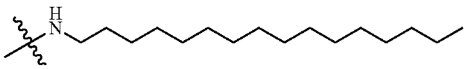
$R_1$ = 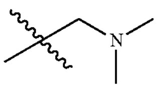 [SMILES: *CN(C)C] $R_2$ = 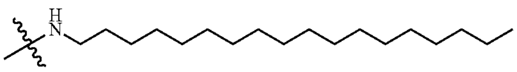

-continued
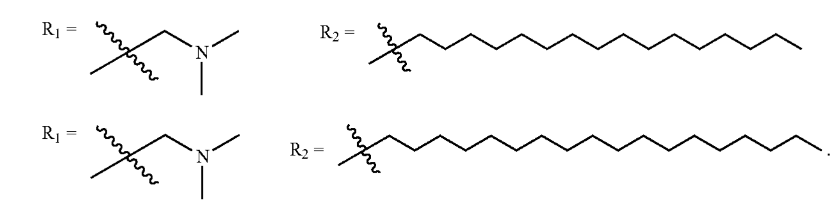
13. The pt(IV) complex of claim 1, having the structure of
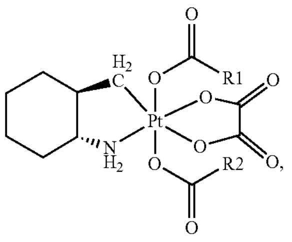
wherein:
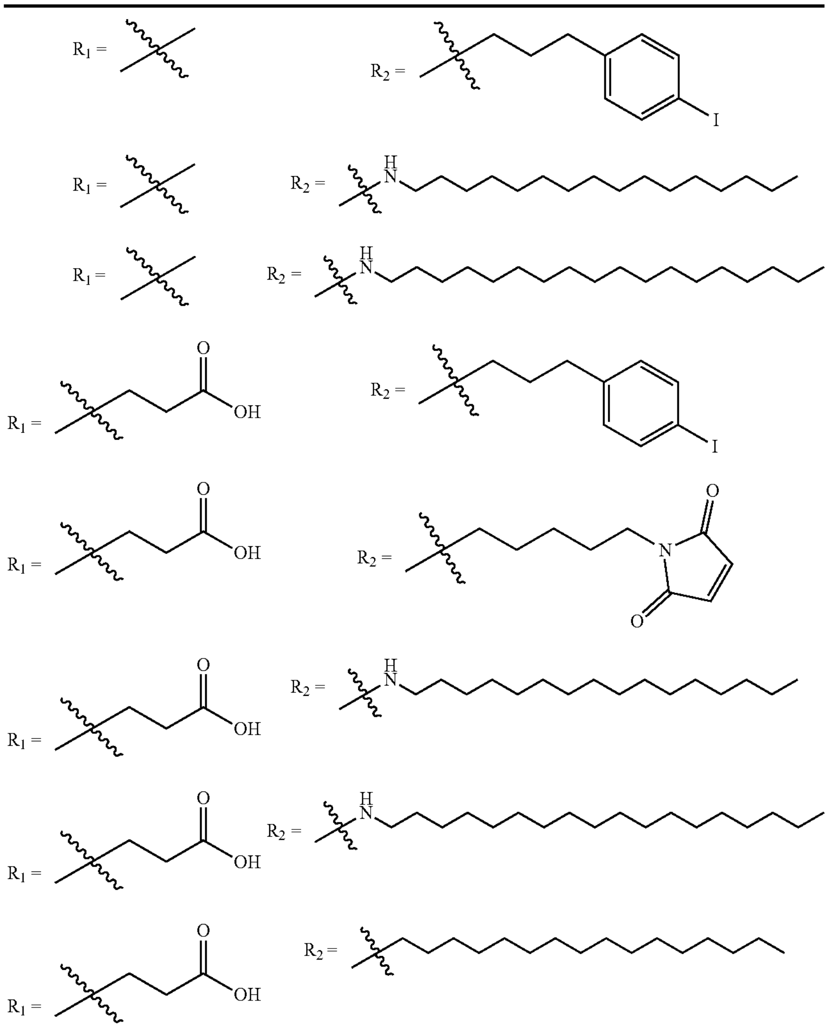

-continued
| | |
|---|---|
| $R_1$ = 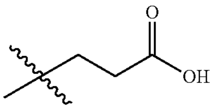 | $R_2$ = 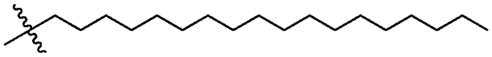 |
| $R_1$ = 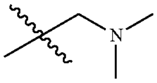 [SMILES: *CN(C)C] | $R_2$ = 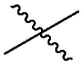 |
| $R_1$ = 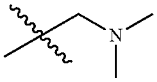 [SMILES: *CN(C)C] | $R_2$ = 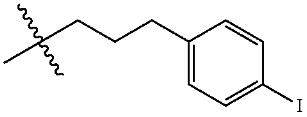 |
| $R_1$ = 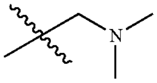 [SMILES: *CN(C)C] | $R_2$ = 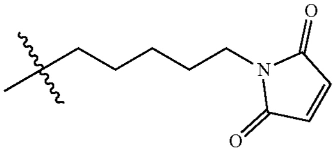 |
| $R_1$ = 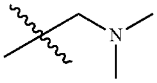 | $R_2$ = 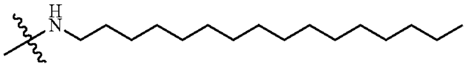 |
| $R_1$ = 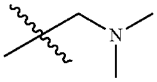 [SMILES: *CN(C)C] | $R_2$ = 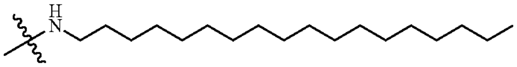 |
| $R_1$ = 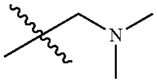 [SMILES: *CN(C)C] | $R_2$ = 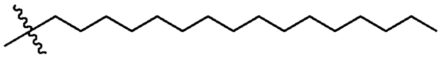 |
| $R_1$ = 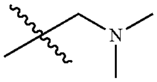 [SMILES: *CN(C)C] | $R_2$ = 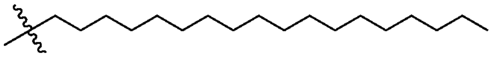 |
* * * * *